United States Patent [19]
Dean et al.

[11] Patent Number: 5,985,558
[45] Date of Patent: Nov. 16, 1999

[54] ANTISENSE OLIGONUCLEOTIDE COMPOSITIONS AND METHODS FOR THE INIBITION OF C-JUN AND C-FOS

[75] Inventors: Nicholas M. Dean, Encinitas; Robert McKay, San Diego; Loren Miraglia, Encinitas; Brenda Baker, Carlsbad, all of Calif.

[73] Assignee: Isis Pharmaceuticals Inc., Carlsbad, Calif.

[21] Appl. No.: 08/837,201

[22] Filed: Apr. 14, 1997

[51] Int. Cl.$^6$ .............. C12Q 1/68; C07H 21/04; C12N 15/85; C12P 19/34
[52] U.S. Cl. .............. 435/6; 435/91.1; 435/325; 435/366; 435/375; 536/23.1; 536/24.31; 536/24.5
[58] Field of Search ................ 514/44; 435/6, 435/325, 366, 375, 91.1; 536/23.1, 24.5, 24.31, 21.33

[56] References Cited

U.S. PATENT DOCUMENTS

| | | | |
|---|---|---|---|
| 4,689,320 | 8/1987 | Kaji | 514/44 |
| 4,806,463 | 2/1989 | Goodchild et al. | 435/5 |
| 4,835,263 | 5/1989 | Nguyen et al. | 536/27 |
| 5,004,810 | 4/1991 | Draper | 536/27 |
| 5,087,617 | 2/1992 | Smith | 514/44 |
| 5,098,890 | 3/1992 | Gewirtz et al. | 514/44 |
| 5,135,917 | 8/1992 | Burch | 514/44 |
| 5,138,045 | 8/1992 | Cook et al. | 536/27 |
| 5,166,195 | 11/1992 | Ecker | 514/44 |
| 5,194,428 | 3/1993 | Agrawal et al. | 514/44 |
| 5,212,295 | 5/1993 | Cook | 536/26.7 |
| 5,218,105 | 6/1993 | Cook et al. | 536/25.31 |
| 5,242,906 | 9/1993 | Pagano et al. | 514/44 |
| 5,264,423 | 11/1993 | Cohen et al. | 514/44 |
| 5,276,019 | 1/1994 | Cohen et al. | 514/44 |
| 5,286,717 | 2/1994 | Cohen et al. | 514/44 |
| 5,378,825 | 1/1995 | Cook et al. | 536/23 |
| 5,386,023 | 1/1995 | Sanghvi et al. | 536/25.3 |
| 5,457,191 | 10/1995 | Cook et al. | 536/27.13 |
| 5,459,255 | 10/1995 | Cook et al. | 536/27.13 |
| 5,512,438 | 4/1996 | Ecker | 435/6 |
| 5,521,302 | 5/1996 | Cook | 536/25.31 |
| 5,539,082 | 7/1996 | Nielsen et al. | 530/300 |
| 5,541,307 | 7/1996 | Cook et al. | 536/23.1 |
| 5,554,746 | 9/1996 | Rafikumar et al. | 540/200 |
| 5,571,902 | 11/1996 | Ravikumar et al. | 536/22.1 |
| 5,578,718 | 11/1996 | Cook et al. | 536/27.21 |
| 5,585,479 | 12/1996 | Hoke et al. | 536/24.5 |
| 5,587,361 | 12/1996 | Cook et al. | 514/44 |
| 5,593,974 | 1/1997 | Rosenberg et al. | 514/44 |
| 5,602,156 | 2/1997 | Kohn et al. | 514/359 |

FOREIGN PATENT DOCUMENTS

| | | |
|---|---|---|
| WO 92/20823 | 11/1992 | WIPO . |
| WO 93/24510 | 12/1993 | WIPO . |
| WO 95/02051 | 1/1995 | WIPO . |
| WO 95/03323 | 2/1995 | WIPO . |
| WO 95/03324 | 2/1995 | WIPO . |
| WO 96/32496 | 10/1996 | WIPO . |
| WO 96/34008 | 10/1996 | WIPO . |
| WO 96/39531 | 12/1996 | WIPO . |

OTHER PUBLICATIONS

Su et al., c–fos is a positive regulator of carcinogen enhancement of adenovirus transformation, Oncogene, vol. 10 (10), pp. 2037–2049, May 1995.

Rojanasakul et al., Antisense oligonucleotidde therapeutics: drug delivery and targeting, Advanced Drug Delivery Reviews, vol. 18, pp. 115–131, 1996.

Gewirtz et al., Facilitating oligonucleotide delivery: helping antisense deliver on its promise, Proc. Natl. Acad. Sci., vol. 93, pp. 3161–3163, Apr. 1996.

Monia et al., Evaluation of 2'–modified oligonucleotides containing 2' deoxy gaps as antisense inhibitors of gene expression., J. Biol. Chem., vol. 268 (19), pp. 14514–14522, Jul. 1993.

Nieborowska–Skorska et al., Oncogene targeted antisense oligodeoxynucleotides combined with chemotherapy or immunotherapy: A new approach to tumor treatment?, Folla Histoch. et Cytobio, vol. 32 (1), pp. 35–40, 1994.

James, Towards gene inhibition therapy: a review of progress and prospectsin the field of antiviral antisense nucleic acids and ribozymes, Antiviral Chemistry & Chemotherapy, vol. 2 (4), pp. 191–214, 1991.

Martin, Ein neuer zugang zu 2'–O–alkylribonucleosiden und eigenschaften deren oligonucleotide, Helv. Chim. Acta, vol. 78, pp. 486–504, 1995.

Protocols for Oligonucleotide Conjugates (Methods in Molecular Biology, vol. 26) Agrawal, S., ed., Humana Press, Totowa, NJ, 1994.

The Merck Manual of Diagnosis and Therapy, 15th Ed., pp. 1206–1228, Berkow et al., eds., Rahay, N.J., 1987.

Angel and Herrlich, Chapter 1, and Schuermann, Chapter 2 in: The FOS and JUN Families of Proteins, Angel and Herrich, eds., pp. 3–35, CRC Press, Boac Raton, FL, 1994.

Molecular Biology of the Cell, Alberts et al., eds., pp. 331–332, Garland Publishing Inc., New York, 1983.

Molecular Biology of the Cell, Alberts et al., eds., pp. 411–415 Garland Publishing Inc., New York, 1983.

Molecular Biology of the Cell, Alberts et al., eds., Chapter 16 pp. 891–950, Garland Publishing, Inc., New York, 1983.

(List continued on next page.)

*Primary Examiner*—Nancy Degen
*Assistant Examiner*—Andrew Wang
*Attorney, Agent, or Firm*—Law Offices of Jane Massey Licata

[57] ABSTRACT

Compositions and methods for the treatment and diagnosis of diseases or disorders amenable to treatment through modulation of Activating Protein 1 (AP-1) expression are provided. In accordance with various embodiments of the present invention, oligonucleotides are provided which are specifically hybridizable with c-fos or c-jun, the genes encoding c-Fos or c-Jun, respectively. In a preferred embodiment, a method of modulating the metastasis of malignant tumors via modulation of one or more of the AP-1 subunits is provided; this method can be effected using the oligonucleotides of the invention or any other agent which modulates AP-1 or AP-1-mediated transcription.

44 Claims, No Drawings

OTHER PUBLICATIONS

Angel and Karin, "The role of Jun, Fos and the AP–1 complex in cell–proliferation and transformation", Biochim. Biophys. Acta, 1991, 1072, 129.

Bailly et al., "PCR–based development of DNA substrates containing modified bases: An efficient system for investigating the role of the exocyclic groups in chemical and structural recognition by minor groove binding drugs and proteins", Proc. Natl. Acad. Sci. U.S.A., 1996, 93:13623.

Bernhard et al. "Direct evidence linking expression of matrix metalloproteinase 9 (92–kDa gelatinase/collagenase) to the metastatic phenotype in transformed rat embryo cells", Proc. Natl. Acad. Sci. (U.S.A.), 1994, 91, 4293.

Binetruy et al., "Ha–Ras augments c–Jun activity and stimulates phosphorylation of its activation domain", Nature, 1991, 351, 122.

Birkedal–Hansen, "Proteolytic remodeling of extracellular matrix", Current Op. Biol., 1995, 7, 728.

Blume and Cevc, "Liposomes for the sustained drug release in vivo", Biochem. et Biophys. Acta, 1990, 1029, 91.

Bohmann et al., "Human Proto–Oncogene c–jun Encodes a DNA Binding Protein with Structural and Functional Properties of Transcription Factor AP–1", Science, 1987, 238, 1386; Angel et al., Nature, 1988, 332, 166.

Brigstock et al,. "Species–Specific High Molecular Weight Forms of Basic Fibroblast Growth Factor", Growth Factors, 1990, 4, 45.

Chen et al., "Antisense oligodeoxynucleotides to c–jun inhibits proliferation of transformed NIH 3T3 cells induced by E5a of HPV–11", Cancer Lett., 1994, 856, 119.

Chonn and Cullis, "Recent advances in liposomal drug–delivery systems", Current Op. Biotech., 1995, 6, 698.

Cobb and Goldsmith, "How MAP Kinases Are Regulated", J. Biol. Chem., 1995, 270, 14843.

Crooke et al., "Pharmacokinetic Properties of Several Novel Oligonucleotide Analogs in Mice", J. Pharmacol. Exp. Ther., 1996, 277, 923.

Curran et al., "Isolation and characterization of the c–fos–(rat) cDNA and analysis of post–translational modification in vitro", Oncogene, 1987, 2:79.

DeVirgilio et al., "Cloning and Disruption of a Gene Required for Growth on Acetate but not on Ethanol: the Acetyl–Coenzyme A Synthetase Gene of Saccrharomyces cerevisiae", Yeast, 1992, 8, 1043.

Ettinger et al., "Intrathecal Methotrexate Overdose Without Neurotoxicity", 1978, Cancer, 41, 1270, 1978.

Ewel et al., "Polyinosinic–Polycytidylic Acid Complexed with Poly–L–lysine and Carboxymethylcelulose in combination with Interleukin 2 in Patients with Cancer: Clinical and Immunological Effects", Cancer Research, 1992, 52:3005.

Fraley et al., "New generation in liposomes: the engineering of an efficient vehicle for intracellular delivery of nucleic acids", Trends in Biochem. Sci., 1981, 6, 77.

French et al., "Expression of two related nonstructural proteins of bluetongue virus (BTV) type 10 in insect cells by a recombinant bacullovirus: production of polyclonal ascitic fluid and characterization of the gene product in BTV–infected BHK cells", J. Virol., 1989, 63, 3270.

Gao et al., "Cloning and characterization of a mouse gene with homology to the human von Hippel–Lindau Disease tumor suppressor gene: implications for the potential organization of the human von Hippel–Lindau disease gene", Cancer Res., 1995, 55, 743.

Gebeyehu, G., "Novel biotinylated nucleotide—analogs for labeling and colorimetric detection of DNA", et al., Nucleic Acids Res., 1987, 15, 4513.

Gelbert et al., "Analysis of GPT activity in mammalian cells with a chromosomally integrated shuttle vector containing altered gpt genes", Somat. Cell. Mol. Genet., 1990, 16, 173.

Gillardon et al., "Inhibition of c–Fos protein expression in rat spinal cord by antisense oligodeoxynucleotide superfusion", Eur. J. Neurosci., 1994, 6, 880.

Gillardon et al., "Expression of c–Fos and c–Jun in the cornea, lens and retina after ultraviolet irradiation of the rat eye and effects of topical antisense oligodeoxynucleotides", British J. Ophthal., 1995, 79, 277.

Gillardon et al., "Inhibition of c–Fos epxression in the UV–irradiated epidermis by topical application of antisense oligodeoxynucleotides suppresses activation of proliferating cell nuclear antigen", Carcinogenesis, 1995, 16, 1853.

Gold and Stormo, Chapter 78 in: *Escherichia coli* and *Salmonella typhimurium*: Cellular and Molecular Biology, vol. 2, p. 1303, Neidhardt et al., eds., American Socieyt for Microbiology, Washington, D.C., 1987.

Gum et al., "Stimulation of 92–kDa gelatinase B promoter activity by ras in mitogen–activated protein kinase kinase 1–independent and requires multiple transcription factor binding sites including closely spaced PEA3/ets and AP–1 sequences", J. Biol. Chem., 1996, 271, 10672.

Hanvey et al., "Antisense and Antigene properties of peptide nucleic acids", Science, 1992, 258:1481.

Hattori et al., "Structure and chromosomal localization of the functional intronless human JUN protooncogene", Proc. Natl. Acad. Sci. U.S.A., 1988, 85:9148.

Himelstein et al., "Metalloproteinases in tumor progression: the contribution of MMP–9", Invasion & Metastasis, 1994, 14, 246.

Hua et al., "Inhibition of matrix metalloproteinase 9 expression by a ribozyme blocks metastasis in a rat sarcoma model system", Cancer Res., 1996, 56, 5279.

Huhtala et al., "Complete structure of the human gene for 92–kDa type IV collagenase", J. Biol. Chem., 1991, 266:16485.

Kabanov et al., "A new class of antivirals: antisense oligonucleotides combined with a hydrophobic substituent effectively inhibit influenza virus reproduction and synthesis of virus–specific proteins in MDCK cells", FEBS Lett., 1990, 259, 327.

Kanagasundaram et al., "Isolation and characterization of the gene encoding gluconolactonase from Zymomonas mobilis", Biochim. Biophys. Acta, 1992, 1171, 198.

Kemeny et al., "A pilot study of hepatic artery floxuridine combined with systemic 5–fluorouracil and leucovorin", Cancer, 1993, 71:1964.

Kerr et al., "Growth factors regulate transin gene expression by c–fos–dependent and c–fos independent pathways", Science, 1988, 242, 1242.

Kerr et al., "TGF–β1 inhibition of transin/stromelysin gene expression is mediated through a fos binding sequence", Cell, 1990, 61, 267.

Kornberg, A., DNA Replication, pp. 4–7, W.H. Freeman & Co., San Francisco, 1980.

Kornberg, A., DNA Replication, pp. 75–77, W.H. Freeman & Co., San Francisco, 1980.

Lappalainen et al., "Cationic liposomes mediated delivery of antisense oligonucleotides targeted to HPV 16 E7 mRNA in CaSki cells", Antiviral Res., 1994, 23, 119.

Letsinger et al., "Cholesteryl–conjugated oligonucleotides: Synthesis, properties and activity as inhibitors of replication of human immunodeficiency virus in cell culture", Proc. Natl. Acad. Sci. USA, 1989, 86, 6553.

Liu et al., "Suppression of Ischemia–induced fos expression and AP–1 activity by an antisense oligodeoxynucleotide to c–fos mRNA", Ann. Neurol., 1994, 36, 566.

Luer and Hatton, "Vanomycin administration into the cerebrospinal fluid: a review", The Annals of Pharmacotherapy, 1993, 27, 912;.

Mannino et al., "Liposome Mediated Gene Transfer", Biotechniques, 1988, 6, 682.

Manoharan et al., "Cholic acid–oligonucleotide conjugates for antisense applications", Bioorg. Med. Chem. Let., 1994, 4, 1053.

Manoharan et al., "Cehmical modifications to improve upake and bioavailability of Antisense oligonucleotides", Antisense Strategies, Ann. N.Y. Acad. Sci., 1992, 660, 306.

Manoharan et al., "Oligonucleotide conjugates: Alteration of the pharmacokinetic properties of antisense agents", Nucleosides & Nucleotides, 1995, 14, 969.

Manoharan et al., "Lipidic Nucleic Acids", Tetrahedron Lett., 1995, 36, 3651.

Manoharan et al., "Introduction of a lipophilic thioether tether in the minor groove of nucleic acids for antisense applications", Bioorg. Med. Chem. Let., 1993, 3, 2765.

Markussen et al., "Translational control of oskar generates Short OSK, the isoform that induces pole plasm assembly", Development, 1995, 121, 3723.

Martin et al., "A new access to 2'-alkulated ribonucleosides and properties of 2'-O-alkylated oligoribonucleotides", Helv. Chim. Acta, 1995, 78, 486.

McDermott et al., "Structure and lens expression of the gene encldoing chicken βA3/A1–crystallin", Gene, 1992, 117, 193.

Mishra et al., "Improved leishmanicdal effect of phosphorothioate antisense oligonucleotides by LDL–mediated delivery", Biochim. Biophys. Acta, 1995, 1264, 229.

Monaco et al., "Structure of two rat genes coding for closely related rolipram–sensitive cAMP phosphodiesterases", J. Biol. Chem., 1994, 269, 347.

Morishita et al., "Single intraluminal delivery of antisense cdc2 kinase and proliferating–cell nuclear antigen oligonucleotides results in chronic inhibition of neointimal hyperplasia", Proc. Natl. Acad. Sci. (U.S.A.), 1993, 90, 8474.

Nielsen et al., "Sequence–selective recognition of DNA by strand displacement with a thymine–substitute polyamide", Science, 191, 254, 1497.

Oberhauser et al., "Effective incorporation of 2'-O-methyl-oligoribonucleotides into liposomes and enhanced cell association through modification with thiocholesterol", Nucl. Acids Res., 1992, 20, 533.

Olsen et al., "Inhibition of protein kinse–A by overexpression of the cloned human protein kinase inhibitor", Mol. Endocrinol., 1991, 5, 1246.

Perri et al., "Interactions of plasmid–encoded relication initiation proteins with the origin of DNA replication in the broad host range plasmid RK2", J. Biol. Chem., 1991, 266, 12536.

Pushpa–Rekha et al., "Rat phosholipid–hydroperoxide glutathione peroxidase", J. Biol. Chem., 1995, 270, 26993.

Raitano et al., The bcr–abl leukemia oncogene activates jun kinase and requires jun for transformation, Proc. Natl. Acad. Sci. (USA), 1995, 92, 11746.

Rogers et al., "Alternative splicing dictates translational start in Epstein–Barr virus transcripts", EMBO J., 1990, 9, 2273.

Rubenstein et al., "Antisense Oligonucleotide intralesional therapy for human PC–3 prostate tumors carried in athymic nude mice", J. Surg. Oncol., 1996, 62:194.

Ruoslahti, "How Cancer Spreads", Sci. Amer., 1996, 275, 72.

Ryder et al., "Induction of protooncogene c–jun by serum growth factors", Proc. Natl. Acad. Sci. U.S.A., 1988, 85:8464.

Sakai et al., "Structure and expression of the rat c–jun messenger RNA: tissue distribution and increase during chemical hepatocarcinogenesis", Cancer Res., 1989, 49:5633.

Saison–Behmoaras et al., "Short modified antisense oligonucleotdes directed gainst Ha–ras point mutation induce selective cleavage of the mRNA and inhibit T24 cells proliferation", EMBO J., 1991, 10, 111.

Sambrook et al., Molecular Cloning. A Laboratory Manual, vol. 2, p. 10.59, Cold Spring Harbor Laboratory Press, 1989.

Sato et al., "Regulatory mechanism of 92 kDa type IV collagenase expression which is associated with invasiveness of tumor cells", Oncogene, 1993, 8:395.

Saul et al., "celB, a gene coding for a bifunctional cellulase from the extreme thermophile 'Caldocellum sacharlyticum'", Appl. Environ. Microbiol., 1990, 56, 3117.

Shaw, "Treatment of intractable cancer pain by electronically controlled parenteral infusion of analgesic drugs", Cancer, 1993, 72(11) Suppl., 3416.

Shea et al., "Synthesis, hybridization properties and antiviral activity of lipid–oligodeoxynucleotide conjugates", Nucl. Acid Res., 1990, 18, 3777.

Smeal et al., "Oncogenic and transcriptional cooperation with Ha–Ras requires phosphorylation of c–jun on serines 63 and 73", Nature, 1991, 354, 494.

Soprano et al., "Use of antisense oligomers to study the role of c–jun in $G_1$ progression", Ann. N. Y. Acad. Sci., 1992, 660, 231.

Stetler–Stevenson et al., "Tumor cell interactions with the extracelular matrix during invasion and metastasis", Annu. Rev. Cell Biol., 1993, 9, 541.

Svinarchuk et al., "Inhibition of HIV proliferation in MT–4 cells by antiense oligonucleotide conjugated to lipophilic gorups", Biochimie, 1993, 75, 49.

Van Beveren et al., "Analysis of FB–J–MuSV provirus and c–fos (mouse) gene reveals that viral and cellular fos gene products have different carboxy termini", Cell, 1983, 32:1241.

Van Straaten et al., "Complete nucleotide sequence of a human c–onc gene: deduced amino acid sequence of the human c–fos protein", Proc. Natl. Acad. Sci. U.S.A., 1983, 80:3183.

Whitesell et al., "Stability, clearance and disposition of intraventricularly administered oligodeoxynucleotides: Implications for therapeutic application within the central nervous system", Proc. Natl. Acad. Sci. (USA), 1993, 90, 4665.

Yaida et al., "Distribution of phosphodiester and phosphorotioate oligonucleotides in rat brain after intraventricular and intrahippocampal administration determined by in situ hybridization", Regul. Pept., 1995, 598, 193.

Yaoita et al., "Xenopus laevis α and β thyroid hormone receptors", Proc. Natl. Acad. Sci. USA, 1990, 87, 7090.

Zimm et al., "Cerbrospinal fluid pharmacokinetics of intraventricular and intravenous aziridinylbenzoquinone", Cancer Research, 1984, 44, 1698.

ANTISENSE OLIGONUCLEOTIDE COMPOSITIONS AND METHODS FOR THE INIBITION OF C-JUN AND C-FOS

FIELD OF THE INVENTION

The present invention provides compositions and methods for modulating levels of the c-fos and c-jun genes, which encode the c-Fos and c-Jun subunits of AP-1, respectively. In vivo, AP-1, or transcription factor activating protein 1, is a heterogenous mixture of heterodimers of several related protein subunits including, in addition to c-Fos and c-Jun, FosB, Fra-1, Fra-2, c-Jun, JunB, JunD, etc. (The FOS and JUN *Families of Proteins,* Angel and Herrlich, eds., CRC Press, Boca Raton, Fla., 1994). AP-1 has been implicated in abnormal cell proliferation and tumor formation, events that thus might be controlled by modulating the expression of c-fos and/or c-jun. The invention is further directed to therapeutic, diagnostic, and research based reagents and methods for evaluating and treating disease states or disorders which result from and/or respond positively to modulation of one or more AP-1 subunits. Such disease states and disorders include those involving the hyperproliferation of cells such as, e.g., a tumor (neoplasm) or malignant cancer. Inhibition of AP-1-mediated hyperproliferation of cells, and corresponding prophylactic, palliative and therapeutic effects result from treatment with the oligonucleotides of the invention.

BACKGROUND OF THE INVENTION

Transcription factors play a central role in the expression of specific genes upon stimulation by extracellular signals, thereby regulating a complex array of biological processes. Members of the family of transcription factors termed AP-1 (activating protein-1) alter gene expression in response to growth factors, cytokines, tumor promoters, carcinogens and increased expression of certain oncogenes. Growth factors and cytokines exert their function by binding to specific cell surface receptors. Receptor occupancy triggers a signal transduction cascade to the nucleus. In this cascade, transcription factors such as AP-1 execute long term responses to the extracellular factors by modulating gene expression. Such changes in cellular gene expression lead to DNA synthesis, and eventually the formation of differentiated derivatives (Angel and Karin, *Biochim. Biophys. Acta,* 1991, 1072, 129).

In general terms, AP-1 denotes one member of a family of related heterodimeric transcription factor complexes found in eukaryotic cells or viruses. However, as used herein, "AP-1" specifically refers to the heterodimer formed of c-Fos and c-Jun (Angel and Herrlich, Chapter 1, and Schuermann, Chapter 2 in: *The FOS and JUN Families of Proteins,* Angel and Herrlich, eds., pp. 3–35, CRC Press, Boca Raton, Fla., 1994; Bohmann et al., *Science,* 1987, 238, 1386; Angel et al., *Nature,* 1988, 332, 166). These two proteins are products of the c-fos and c-jun proto-oncogenes, respectively. Repression of expression of either c-fos or c-jun, or of both proto-oncogenes, and the resultant inhibition of the formation of c-Fos and c-Jun proteins, is desirable for the inhibition of cell proliferation, tumor formation and tumor growth.

The phosphorylation of proteins plays a key role in the transduction of extracellular signals into the cell. Mitogen-activated protein (MAP) kinases, enzymes which effect such phosphorylations are targets for the action of growth factors, hormones, and other agents involved in cellular metabolism, proliferation and differentiation (Cobb et al., *J. Biol. Chem.,* 1995, 270, 14843). MAP kinases are themselves activated by phosphorylation catalyzed by, e.g., receptor tyrosine kinases, G protein-coupled receptors, protein kinase C (PKC), and the apparently MAP kinase dedicated kinases MEK1 and MEK2. MAP kinases include, but are not limited to, ERK1, ERK2, two isoforms of ERK3, ERK4 (ERK stands for "extracellular signal-regulated protein kinase), Jun N-terminal kinases/stress-activated protein kinases (JNKs/SAPKs), p38/HOG1, p57 MAP kinases, MKK3 (MAP kinase kinase 3) and MKK4 (MAP kinase kinase 4, also known as SAPK/ERK kinase (SEK) or JNK kinase (JNKK)) (Cobb et al., *J. Biol. Chem.,* 1995, 270, 14843, and references cited therein). In general, MAP kinases are involved in a variety of signal transduction pathways (sometimes overlapping and sometimes parallel) that function to convey extracellular stimuli to protooncogene products to modulate cellular proliferation and/or differentiation.

One of the signal transduction pathways involves the MAP kinases Jun kinase 1 and Jun kinase 2 which are responsible for the phosphorylation of specific sites (Serine 63 and Serine 73) on c-Jun. Phosphorylation of these sites potentiates the ability of AP-1 to activate transcription (Binetruy et al., *Nature,* 1991, 351, 122; Smeal et al., *Nature,* 1991, 354, 494). At least one human leukemia oncogene has been shown to enhance Jun N-terminal Kinase (JNK) function (Raitano et al., *Proc. Natl. Acad. Sci.* (USA), 1995, 92, 11746), thus indirectly demonstrating a role for AP-1 in cellular hyperproliferation and tumorigenesis. Cellular hyperproliferation in an animal can have several outcomes. Hyperproliferating cells might be attacked and killed by the animal's immune system before a tumor can form. Tumors are abnormal growths resulting from the hyperproliferation of cells. Cells that proliferate to excess but stay put form benign tumors, which can typically be removed by local surgery. In contrast, malignant tumors or cancers comprise cells that are capable of undergoing metastasis, i.e., a process by which hyperproliferative cells spread to, and secure themselves within, other parts of the body via the circulatory or lymphatic system (see, generally, Chapter 16 In: *Molecular Biology of the Cell,* Alberts et al., eds., pp. 891–950, Garland Publishing, Inc., New York, 1983). Using the oligonucleotides of the invention, it has surprisingly been discovered that several genes encoding enzymes required for metastasis are positively regulated by AP-1. Accordingly, inhibition of expression of c-fos and/or c-jun serves as a means to modulate the metastasis of malignant tumors. A method of modulating one or more metastatic events using the oligonucleotides of the invention is thus herein provided.

RELEVANT ART

Soprano et al. (*Ann. N. Y. Acad. Sci.,* 1992, 660, 231) have used antisense oligodeoxynucleotides targeted to c-jun mRNA to study their ability to inhibit DNA synthesis and cell division.

Liu et al. (*Ann. Neurol.,* 1994, 36, 566) describe the suppression of c-fos by intraventricular infusion of an antisense oligodeoxynucleotide targeted to c-fos mRNA.

Chen et al. (*Cancer Lett.,* 1994, 85, 119) describe repression of c-jun expression by antisense oligodeoxynucleotides resulting in the inhibition of cell proliferation in E5a transformed cells.

Gillardon et al. describe the topical application of c-fos antisense oligodeoxynucleotides to the rat spinal cord (*Eur. J. Neurosci.,* 1994, 6, 880) ultraviolet (UV)-exposed rat eyes (*British J. Ophthal.,* 1995, 79, 277) and UV-irradiated rat skin (*Carcinogenesis,* 1995, 16, 1853).

U.S. Pat. No. 5,602,156, which issued Feb. 11, 1997, to Kohn et al., discloses non-oligonucleotide compositions and methods for inhibiting the expression of two metalloproteinases, MMP-1 and MMP-2.

International Publication Number WO 95/02051, published Jan. 19, 1995, discloses antisense oligonucleotides targeted to the mRNA of c-fos and c-jun.

International Publication Number WO 95/03323, published Feb. 2, 1995, discloses antisense nucleic acids which are complementary to the polynucleotide encoding a polypeptide which is capable of phosphorylating the c-jun N-terminal activation domain. Also provided are methods for treating a cell proliferative disorder associated with said polypeptide.

International Publication Number WO 95/03324, published Feb. 2, 1995, describes a polypeptide which phosphorylates the c-jun N-terminal activation domain. This publication also discloses a polynucleotide sequence encoding the polypeptide.

To date, there are no known therapeutic agents which effectively inhibit gene expression of c-fos and/or c-jun.

Furthermore, there are to date no known therapeutic agents that modulate the metastasis of malignant cells. The compositions and methods of the invention overcome these limitations. Further objectives of the invention are apparent from the present disclosure.

SUMMARY OF THE INVENTION

In accordance with the present invention, oligonucleotides are provided which specifically hybridize with nucleic acids encoding c-Fos or c-Jun. Certain oligonucleotides of the invention are designed to bind either directly to mRNA transcribed from, or to a selected DNA portion of, the respective gene, thereby modulating the amount of protein translated from a c-fos or c-jun mRNA and/or the amount of mRNA transcribed from a c-fos or c-jun gene, respectively. Such modulation can, in turn, effect the modulation of enzymes and cellular processes involved in the metastasis of malignant cells.

Oligonucleotides may comprise nucleotide sequences sufficient in identity and number to effect specific hybridization with a particular nucleic acid. Such oligonucleotides are commonly described as "antisense." Antisense oligonucleotides are commonly used as research reagents, diagnostic aids, and therapeutic agents.

It has been discovered that the c-fos and c-jun genes, encoding the c-Fos and c-Jun proteins, respectively, are particularly amenable to this approach. As a consequence of the association between cellular proliferation and AP-1 (the heterodimer of c-Fos and c-Jun) expression, modulation of the expression of c-fos and/or c-jun leads to modulation of AP-1, and, accordingly, modulation of cellular proliferation. Such modulation is desirable for treating or modulating various hyperproliferative disorders or diseases, such as various cancers. Such inhibition is further desirable for preventing or modulating the development of such diseases or disorders in an animal suspected of being, or known to be, prone to such diseases or disorders. If desired, modulation of one subunit can be combined with modulation of the subunit of AP-1 in order to achieve a requisite degree of effect upon AP-1-mediated transcription.

Methods of modulating the expression of c-Fos or c-Jun proteins comprising contacting animals with oligonucleotides specifically hybridizable with a c-fos or c-jun gene, respectively, are herein provided. These methods are believed to be useful both therapeutically and diagnostically as a consequence of the association between AP-1 expression and cellular proliferation. These methods are also useful as tools, for example, in the detection and determination of the role of AP-1 protein expression in various cell functions and physiological processes and conditions, and for the diagnosis of conditions associated with such expression and activation.

The present invention also comprises methods of inhibiting AP-1-mediated transcriptional activation using the oligonucleotides of the invention. Methods of treating conditions in which abnormal or excessive AP-1-mediated transcriptional activation and cellular proliferation occur are also provided. These methods employ the oligonucleotides; of the invention and are believed to be useful both therapeutically and as clinical research and diagnostic tools. The oligonucleotides of the present invention may also be used for research purposes. Thus, the specific hybridization exhibited by the oligonucleotides of the present invention may be used for assays, purifications, cellular product preparations and in other methodologies which may be appreciated by persons of ordinary skill in the art.

Methods comprising contacting animals with oligonucleotides specifically hybridizable with nucleic acids encoding c-Fos or c-Jun proteins are herein provided. Such methods can be used to modulate or detect the expression of c-fos or c-jun genes and are thus believed to be useful both therapeutically and diagnostically.

The methods disclosed herein are also useful, for example, as clinical research tools in the detection and determination of the role of AP-1-mediated gene expression in various immune system functions and physiological processes and conditions, and for the diagnosis of conditions associated with their expression. The specific hybridization exhibited by the oligonucleotides of the present invention may be used for assays, purifications, cellular product preparations and in other methodologies which may be appreciated by persons of ordinary skill in the art. For example, because the oligonucleotides of this invention specifically hybridize to nucleic acids encoding c-Fos or c-Jun, sandwich and other assays can easily be constructed to exploit this fact. Detection of specific hybridization of an oligonucleotide of the invention with a nucleic acid encoding a c-Fos or c-Jun protein present in a sample can routinely be accomplished. Such detection may include detectably labeling an oligonucleotide of the invention by enzyme conjugation, radiolabeling or any other suitable detection system. A number of assays may be formulated employing the present invention, which assays will commonly comprise contacting a tissue or cell sample with a detectably labeled oligonucleotide of the present invention under conditions selected to permit hybridization and measuring such hybridization by detection of the label, as is appreciated by those of ordinary skill in the art.

DETAILED DESCRIPTION OF THE INVENTION

The present invention employs oligonucleotides for use in antisense inhibition of the function of RNA and DNA encoding a c-Fos protein or a c-Jun protein. The present invention also employs oligonucleotides which are designed to be specifically hybridizable to DNA or messenger RNA (mRNA) encoding such proteins and ultimately modulating the amount of such proteins transcribed from their respective genes. Such hybridization with mRNA interferes with the normal role of mRNA and causes a modulation of its function in cells. The functions of mRNA to be interfered with include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with mRNA function is modulation of the expression of a c-Fos protein or a c-Jun protein. In the context of this invention, "modulation" means either an increase (stimulation) or a decrease (inhibition) in the expression of a gene. In the context of the present invention, inhibition is the preferred form of modulation of gene expression.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

An oligonucleotide is a polymer of a repeating unit generically known as a nucleotide. An unmodified (naturally occurring) nucleotide has three components: (1) a nitrogenous base linked by one of its nitrogen atoms to (2) a 5-carbon cyclic sugar and (3) a phosphate, esterified to carbon 5 of the sugar. When incorporated into an oligonucleotide chain, the phosphate of a first nucleotide is also esterified to carbon 3 of the sugar of a second, adjacent nucleotide. The "backbone" of an unmodified oligonucleotide consists of (2) and (3), that is, sugars linked together by phosphodiester linkages between the carbon 5 (5') position of the sugar of a first nucleotide and the carbon 3 (3') position of a second, adjacent nucleotide. A "nucleoside" is the combination of (1) a nucleobase and (2) a sugar in the absence of (3) a phosphate moiety (Kornberg, A., *DNA Replication*, pp. 4–7, W. H. Freeman & Co., San Francisco, 1980). The backbone of an oligonucleotide positions a series of bases in a specific order; the written representation of this series of bases, which is conventionally written in 5' to 3' order, is known as a nucleotide sequence. The oligonucleotides in accordance with this invention preferably comprise from about 8 to about 30 nucleotides. It is more preferred that such oligonucleotides comprise from about 15 to 25 nucleotides.

Oligonucleotides may comprise nucleotide sequences sufficient in identity and number to effect specific hybridization with a particular nucleic acid. Such oligonucleotides which specifically hybridize to a portion of the sense strand of a gene are commonly described as "antisense." Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses.

The specificity and sensitivity of oligonucleotides is also harnessed by those of skill in the art for therapeutic uses. For example, the following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of Human Immunodeficiency Virus (HIV). U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to cytomegalovirus (CMV). U.S. Pat. No. 5,098,890 provides oligonucleotides complementary to at least a portion of the mRNA transcript of the human c-myb gene. U.S. Pat. No. 5,242,906 provides antisense oligonucleotides useful in the treatment of latent Epstein-Barr virus (EBV) infections.

It is preferred to target specific genes for antisense attack. "Targeting" an oligonucleotide to the associated nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a foreign nucleic acid from an infectious agent. In the present invention, the target is a cellular gene (c-fos or c-jun) encoding a subunit of AP-1, for which modulation is desired in certain instances. The targeting process also includes determination of a region (or regions) within this gene for the oligonucleotide interaction to occur such that the desired effect, either detection or modulation of expression of the protein, will result. Once the target region have been identified, oligonucleotides are chosen which are sufficiently complementary to the target, i.e., hybridize sufficiently well and with sufficient specificity to give the desired effect.

There are many regions of a gene that may be targeted for antisense modulation: the region of the 5' Cap, a specialized structure that at least partially mediates ribosome binding; the 5' untranslated (noncoding) region (hereinafter, the "5'-UTR"); the translation initiation codon region (hereinafter, the "tIR"); the open reading frame (hereinafter, the "ORF"); the translation termination codon region (hereinafter, the "tTR"); and the 3' untranslated (noncoding) region (hereinafter, the "3'-UTR"), which has at its 3' end a "poly A" tail. As is known in the art, these regions are arranged in a typical messenger RNA molecule in the following order (left to right, 5' to 3'): 5' Cap, 5'-UTR, tIR, ORF, tTR, 3'-UTR, poly A tail. As is also known in the art, although some eukaryotic transcripts are directly translated, many ORFs contain one or more sequences, known as "introns," which are excised from a transcript before it is translated; the expressed (unexcised) portions of the ORF are referred to as "exons" (Alberts et al., *Molecular Biology of the Cell*, pp. 331–332 and 411–415, Garland Publishing Inc., New York, 1983). Furthermore, because many eukaryotic ORFs are a thousand nucleotides or more in length, it is often convenient to subdivide the ORF into, e.g., the 5' ORF region, the central ORF region, and the 3' ORF region. In some instances, an ORF contains one or more sites that may be targeted due to some functional significance in vivo. Examples of the latter types of sites include intragenic stem-loop structures (see, e.g., U.S. Pat. No. 5,512,438) and, in unprocessed mRNA molecules, intron/exon splice sites. Within the context of the present invention, one preferred intragenic site is the region encompassing the translation initiation codon of the open reading frame (ORF) of the gene. Because, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Furthermore, 5'-UUU functions as a translation initiation codon in vitro (Brigstock et al., *Growth Factors,* 1990, 4, 45; Gelbert et al., *Somat. Cell. Mol. Genet.,* 1990, 16, 173; Gold and Stormo, Chapter 78 in: *Escherichia coli and Salmonella typhimurium: Cellular and Molecular Biology,* Vol. 2, p. 1303, Neidhardt et al., eds., American Society for Microbiology, Washington, D.C., 1987). Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions, in order to generate related polypeptides having different amino terminal sequences (Markussen et al., *Development,* 1995, 121, 3723; Gao et al., *Cancer Res.,* 1995, 55, 743; McDermott et al., *Gene,* 1992, 117, 193; Perri et al., *J. Biol. Chem.,* 1991, 266, 12536; French et al., *J. Virol.,* 1989, 63, 3270; Pushpa-Rekha et al., *J. Biol. Chem.,* 1995, 270, 26993; Monaco et al., *J. Biol. Chem.,* 1994, 269, 347; DeVirgilio et al., *Yeast,* 1992, 8, 1043; Kanagasundaram et al., *Biochim. Biophys. Acta,* 1992, 1171, 198; Olsen et al., *Mol. Endocrinol.,* 1991, 5, 1246; Saul et al., *Appl. Environ. Microbiol.,* 1990, 56, 3117; Yaoita et al., *Proc. Natl. Acad. Sci. USA,* 1990, 87, 7090; Rogers et al., *EMBO J.,* 1990, 9, 2273). In the context of the invention, "start codon" and "translation initiation codon" refer to the codon or codons that are used in vivo to initiate translation of an mRNA molecule transcribed from a gene encoding a c-Fos or c-Jun protein, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation region" refer to a portion of such an mRNA or gene that encompasses from about 25 to about 50 contiguous nucleotides in either direction (i.e., 5' or 3') from a translation initiation codon. Similarly, the terms "stop codon region" and "translation termination region" refer to a portion of such an mRNA or gene that encompasses from about 25 to about 50 contiguous nucleotides in either direction (i.e., 5' or 3') from a translation termination codon.

In the context of this invention, the term "oligonucleotide" includes oligonucleotides composed of naturally-occurring nucleobases, sugars and covalent intersugar (backbone) linkages as well as oligonucleotides having non-naturally-occurring portions which function similarly.

Such modified or substituted oligonucleotides may be preferred over native forms because of desirable properties such as, for example, enhanced cellular uptake, enhanced binding to target and increased stability in the presence of nucleases.

Specific examples of some preferred modified oligonucleotides envisioned for this invention include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates and those with $CH_2$—NH—O—$CH_2$, $CH_2$—$N(CH_3)$—O—$CH_2$ [known as a methylene(methylimino) or MMI backbone], $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones, wherein the native phosphodiester backbone is represented as O—P—O—$CH_2$). Also preferred are oligonucleotides having morpholino backbone structures (Summerton and Weller, U.S. Pat. No. 5,034,506). Further preferred are oligonucleotides with NR—C(*)—$CH_2$—$CH_2$, $CH_2$—NR—C(*)—$CH_2$, $CH_2$—$CH_2$—NR—C(*), C(*)—NR—$CH_2$—$CH_2$ and $CH_2$—C(*)—NR—$CH_2$ backbones, wherein "*" represents O or S (known as amide backbones; DeMesmaeker et al., WO 92/20823, published Nov. 26, 1992). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., *Science,* 1991, 254, 1497; U.S. Pat. No. 5,539,082).

The oligonucleotides of the invention may additionally or alternatively include nucleobase modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-methylcytosine, 5-hydroxymethylcytosine (HMC), glycosyl HMC and gentiobiosyl HMC, as well synthetic nucleobases, e.g., 2-aminoadenine, 2-thiouracil, 2-thiothymine, 5-bromouracil, 5-hydroxymethyluracil, 8-azaguanine, 7-deazaguanine, $N^6$(6-aminohexyl)adenine and 2,6-diaminopurine (Kornberg, A., *DNA Replication,* pp. 75–77, W. H. Freeman & Co., San Francisco, 1980; Gebeyehu, G., et al., *Nucleic Acids Res.,* 1987, 15, 4513).

The oligonucleotides of the invention may additionally or alternatively comprise substitutions of the sugar portion of the individual nucleotides. For example, oligonucleotides may also have sugar mimetics such as cyclobutyls in place of the pentofuranosyl group. Other preferred modified oligonucleotides may contain one or more substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification, particularly for orally deliverable pharmaceutical compositions, is 2'-methoxyethoxy [2'—O—$CH_2CH_2OCH_3$, also known as 2'—O—(2-methoxyethyl)] (Martin et al., *Helv. Chim. Acta,* 1995, 78, 486). Other preferred modifications include 2'-methoxy (2'—O—CH$_3$), 2'-propoxy (2'—OCH$_2$CH$_2$CH$_3$) and 2'-fluoro (2'—F).

Similar modifications may also be made at other positions on the oligonucleotide, particularly the 3' position of the sugar on the 3' terminal nucleotide and the 5' position of 5' terminal nucleotide. The 5' and 3' termini of an oligonucleotide may also be modified to serve as points of chemical conjugation of, e.g., lipophilic moieties (see immediately subsequent paragraph), intercalating agents (Kuyavin et al., WO 96/32496, published Oct. 17, 1996; Nguyen et al., U.S. Pat. No. 4,835,263, issued May 30, 1989) or hydroxyalkyl groups (Helene et al., WO 96/34008, published Oct. 31, 1996).

Other positions within an oligonucleotide of the invention can be used to chemically link thereto one or more effector groups to form an oligonucleotide conjugate. An "effector group" is a chemical moiety that is capable of carrying out a particular chemical or biological function. Examples of such effector groups include, but are not limited to, an RNA cleaving group, a reporter group, an intercalator, a group for improving the pharmacokinetic properties of an oligonucleotide, or a group for improving the pharmacodynamic properties of an oligonucleotide and other substituents having similar properties. A variety of chemical linkers may be used to conjugate an effector group to an oligonucleotide of the invention. As an example, U.S. Pat. No. 5,578,718 to Cook et al. discloses methods of attaching an alkylthio linker, which may be further derivatized to include additional groups, to ribofuranosyl positions, nucleosidic base positions, or on internucleoside linkages. Additional methods of conjugating oligonucleotides to various effector groups are known in the art; see, e.g., *Protocols for Oligonucleotide Conjugates* (*Methods in Molecular Biology*, Volume 26) Agrawal, S., ed., Humana Press, Totowa, N.J., 1994.

Another preferred additional or alternative modification of the oligonucleotides of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The N$^6$ position of a purine nucleobase may also be utilized to link a lipophilic moiety to an oligonucleotide of the invention (Gebeyehu et al., *Nucleic Acids Res.*, 1987, 15, 4513). Such lipophilic moieties include but are not limited to a cholesteryl moiety (Letsinger et al., *Proc. Natl. Acad. Sci.* USA, 1989, 86, 6553), cholic acid (Manoharan et al., *Bioorg. Med. Chem. Let.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923). oligonucleotides comprising lipophilic moieties, and methods for preparing such oligonucleotides, are disclosed in U.S. Pat. No. 5,138,045, No. 5,218,105 and No. 5,459,255, the contents of which are hereby incorporated by reference.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

The present invention also includes oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361, issued Dec. 24, 1996) and those having substantially chirally pure (Sp or Rp) alkylphosphonate, phosphoamidate or phosphotriester linkages (Cook, U.S. Pat. No. 5,212,295, issued May 18, 1993; Cook, U.S. Pat. No. 5,521,302, issued May 28, 1996).

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for the target RNA molecule but are unable to support nuclease activity (e.g., 2'-fluoro- or 2'-methoxyethoxy substituted). Other chimeras include "wingmers," that is, oligonucleotides in which the 5' portion of the oligonucleotide serves as a substrate for, e.g., RNase H, whereas the 3' portion is modified in such a fashion so as to have greater affinity for the target RNA molecule but is unable to support nuclease activity (e.g., 2'-fluoro- or 2'-methoxyethoxy substituted), or vice-versa.

The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives. Teachings regarding the synthesis of particular modified oligonucleotides are hereby incorporated by reference from the following U.S. patents or pending patent applications, each of which is commonly assigned with this application: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having b-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties, attached at any of a variety of positions of the nucleoside; and U.S. Pat. No. 5,587,361, drawn to oligonucleotides having phosphorothioate linkages of high chiral purity.

The oligonucleotides of the present invention can be utilized as therapeutic compounds, diagnostic tools and as research reagents and kits. The term "therapeutic uses" is intended to encompass prophylactic, palliative and curative uses wherein the oligonucleotides of the invention are contacted with animal cells either in vivo or ex vivo. When contacted with animal cells ex vivo, a therapeutic use includes incorporating such cells into an animal after treatment with one or more oligonucleotides of the invention.

For therapeutic uses, an animal suspected of having a disease or disorder which can be treated or prevented by modulating the expression or activity of a c-Fos or c-Jun protein is, for example, treated by administering oligonucleotides in accordance with this invention. The oligonucleotides of the invention can be utilized in pharmaceutical compositions by adding an effective amount of an oligonucleotide to a suitable pharmaceutically acceptable diluent or carrier. Workers in the field have identified antisense, triplex and other oligonucleotide compositions which are capable of modulating expression of genes implicated in viral, fungal and metabolic diseases. Antisense oligonucleotides have been safely administered to humans and several clinical trials are presently underway. It is thus established that oligonucleotides can be useful therapeutic instrumentalities that can be configured to be useful in treatment regimes for treatment of cells, tissues and animals, especially humans.

The oligonucleotides of the present invention can be further used to detect the presence of c-fos- or c-jun-specific nucleic acids in a cell or tissue sample. For example, radiolabeled oligonucleotides can be prepared by $^{32}p$ labeling at the 5' end with polynucleotide kinase (Sambrook et al., *Molecular Cloning. A Laboratory Manual*, Vol. 2, p. 10.59, Cold Spring Harbor Laboratory Press, 1989). Radiolabeled oligonucleotides are then contacted with cell or tissue samples suspected of containing c-fos or c-jun message RNAs (and thus c-Fos or c-Jun proteins), and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of tissues to determine the localization, distribution and quantitation of c-Fos or c-Jun proteins for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing a c-Fos or c-Jun gene. Quantitation of the silver grains permits detection of the expression of mRNA molecules encoding these proteins and permits targeting of oligonucleotides to these areas.

Analogous assays for fluorescent detection of expression of c-fos or c-jun nucleic acids can be developed using oligonucleotides of the present invention which are conjugated with fluorescein or other fluorescent tags instead of radiolabeling. Such conjugations are routinely accomplished during solid phase synthesis using fluorescently-labeled amidites or controlled pore glass (CPG) columns. Fluorescein-labeled amidites and CPG are available from, e.g., Glen Research (Sterling, Va.).

The present invention employs oligonucleotides targeted to nucleic acids encoding c-Fos or c-Jun proteins and oligonucleotides targeted to nucleic acids encoding such proteins. Kits for detecting the presence or absence of expression of a c-Fos and/or c-Jun protein may also be prepared. Such kits include an oligonucleotide targeted to an appropriate gene, i.e., a gene encoding a c-Fos or c-Jun protein. Appropriate kit and assay formats, such as, e.g., "sandwich" assays, are known in the art and can easily be adapted for use with the oligonucleotides of the invention. Hybridization of the oligonucleotides of the invention with a nucleic acid encoding a c-Fos or c-Jun protein can be detected by means known in the art. Such means may include conjugation of an enzyme to the oligonucleotide, radiolabelling of the oligonucleotide or any other suitable detection systems. Kits for detecting the presence or absence of a c-Fos or c-Jun protein may also be prepared.

In the context of this invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a decrease or loss of function, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

The formulation of therapeutic compositions and their subsequent administration is believed to be within the skill of those in the art. In general, for therapeutics, a patient in need of such therapy is administered an oligonucleotide in accordance with the invention, commonly in a pharmaceutically acceptable carrier, in doses ranging from 0.01 ug to 100 g per kg of body weight depending on the age of the patient and the severity of the disorder or disease state being treated. Further, the treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the oligonucleotide may either be increased in the event the patient does not respond significantly to current dosage levels, or the dose may be decreased if an alleviation of the symptoms of the disorder or disease state is observed, or if the disorder or disease state has been abated.

In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). See, generally, *The Merck Manual of Diagnosis and Therapy*, 15th Ed., pp. 1206–1228, Berkow et al., eds., Rahay, N.J., 1987). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

In another preferred embodiment of the invention, a first antisense oligonucleotide targeted to c-fos is used in combination with a second antisense oligonucleotide targeted to c-jun in order to modulate AP-1 molecules to a more extensive degree than can be achieved when either oligonucleotide used individually.

Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years. In the case of in individual known or suspected of being prone to a neoplastic or malignant condition, prophylactic effects may be achieved by administration of preventative doses, ranging from 0.01 ug to 100 g per kg of body weight, once or more daily, to once every 20 years.

The pharmaceutical compositions of the present invention may be administered in a number of ways depending upon whether local or systemic treatment is desired and upon the area to be treated. Within the context of the invention, "administration" indicates the topical (including ophthalmic, vaginal, rectal, intranasal, transdermal), oral or parenteral contacting of an oligonucleotide, or pharmaceutical composition comprising an oligonucleotide, with cells, tissues or organs of a mammal including a human. Parenteral administration includes intravenous drip; subcutaneous, intraperitoneal, intravitreal or intramuscular injection; and intrathecal or intraventricular administration as herein described.

Formulations for topical administration may include transdermal patches, ointments, lotions, creams, gels, drops, suppositories, sprays, liquids and powders. Conventional pharmaceutical carriers, nucleic acid carriers, aqueous, powder or oily bases, thickeners and the like may be necessary or desirable in certain instances. Topical administration also includes the delivery of oligonucleotides into the epidermis of a mammal by electroporation (Zewert et al., WO 96/39531, published Dec. 12, 1996).

Compositions for oral administration include powders or granules, suspensions or solutions in water or non-aqueous media, capsules, sachets or tablets. Thickeners, flavoring agents, diluents, emulsifiers, dispersing aids or binders may be desirable.

Intravitreal injection, for the direct delivery of drug to the vitreous humor of a mammalian eye, is described in U.S. Pat. No. 5,595,978, which issued Jan. 21, 1997, and which is assigned to the same assignee as the instant application, the contents of which are hereby incorporated by reference.

Intraluminal drug administration, for the direct delivery of drug to an isolated portion of a tubular organ or tissue (e.g., such as an artery, vein, ureter or urethra), may be desired for the treatment of patients with diseases or conditions afflicting the lumen of such organs or tissues. To effect this mode of oligonucleotide administration, a catheter or cannula is surgically introduced by appropriate means. For example, for treatment of the left common carotid artery, a cannula is inserted thereinto via the external carotid artery. After isolation of a portion of the tubular organ or tissue for which treatment is sought, a composition comprising the oligonucleotides of the invention is infused through the cannula or catheter into the isolated segment. After incubation for from about 1 to about 120 minutes, during which the oligonucleotide is taken up by cells of the interior lumen of the vessel, the infusion cannula or catheter is removed and flow within the tubular organ or tissue is restored by removal of the ligatures which effected the isolation of a segment thereof (Morishita et al., *Proc. Natl. Acad. Sci.* (U.S.A.), 1993, 90, 8474). Antisense oligonucleotides may also be combined with a biocompatible matrix or carrier, such as a hydrogel material, and applied directly to vascular tissue in vivo (Rosenberg et al., U.S. Pat. No. 5,593,974, issued Jan. 14, 1997).

Intraventricular drug administration, for the direct delivery of drug to the brain of a patient, may be desired for the treatment of patients with diseases or conditions afflicting the brain. To effect this mode of oligonucleotide administration, a silicon catheter is surgically introduced into a ventricle of the brain of a human patient, and is connected to a subcutaneous infusion pump (Medtronic Inc., Minneapolis, Minn.) that has been surgically implanted in the abdominal region (Zimm et al., *Cancer Research*, 1984, 44, 1698; Shaw, *Cancer*, 1993, 72(11 Suppl.), 3416). The pump is used to inject the oligonucleotides and allows precise dosage adjustments and variation in dosage schedules with the aid of an external programming device. The reservoir capacity of the pump is 18–20 mL and infusion rates may range from 0.1 mL/h to 1 mL/h. Depending on the frequency of administration, ranging from daily to monthly, and the dose of drug to be administered, ranging from 0.01 $\mu$g to 100 g per kg of body weight, the pump reservoir may be refilled at 3–10 week intervals. Refilling of the pump is accomplished by percutaneous puncture of the self-sealing septum of the pump.

Intrathecal drug administration for the introduction of drug into the spinal column of a patient may be desired for the treatment of patients with diseases of the central nervous system. To effect this route of oligonucleotide administration, a silicon catheter is surgically implanted into the L3-4 lumbar spinal interspace of a human patient, and is connected to a subcutaneous infusion pump which has been surgically implanted in the upper abdominal region (Luer and Hatton, *The Annals of Pharmacotherapy*, 1993, 27, 912; Ettinger et al., 1978, *Cancer*, 41, 1270, 1978; Yaida et al., *Regul. Pept.*, 1995, 59, 193). The pump is used to inject the oligonucleotides and allows precise dosage adjustments and variations in dose schedules with the aid of an external programming device. The reservoir capacity of the pump is 18–20 mL, and infusion rates may vary from 0.1 mL/h to 1 mL/h. Depending on the frequency of drug administration, ranging from daily to monthly, and dosage of drug to be administered, ranging from 0.01 $\mu$g to 100 g per kg of body weight, the pump reservoir may be refilled at 3–10 week intervals. Refilling of the pump is accomplished by a single percutaneous puncture to the self-sealing septum of the pump. The distribution, stability and pharmacokinetics of oligonucleotides within the central nervous system may be followed according to known methods (Whitesell et al., *Proc. Natl. Acad. Sci* (USA), 1993, 90, 4665).

To effect delivery of oligonucleotides to areas other than the brain or spinal column via this method, the silicon catheter is configured to connect the subcutaneous infusion pump to, e.g., the hepatic artery, for delivery to the liver (Kemeny et al., *Cancer*, 1993, 71:1964). Infusion pumps may also be used to effect systemic delivery of oligonucleotides (Ewel et al., *Cancer Research*, 1992, 52:3005; Rubenstein et al., *J. Surg. Oncol.*, 1996, 62:194).

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles and liposomes. A preferred colloidal dispersion system is a plurality of liposomes, artificial membrane vesicles which may be used as cellular delivery vehicles for bioactive agents in vitro and in vivo (Mannino et al., *Biotechniques*, 1988, 6, 682; Blume and Cevc, *Biochem. et Biophys. Acta*, 1990, 1029, 91; Lappalainen et al., *Antiviral Res.*, 1994, 23, 119; Chonn and Cullis, *Current Op. Biotech.*, 1995, 6, 698). It has been shown that large unilamellar vesicles (LUV), which range in size from 0.2–0.4 $\mu$m, can encapsulate a substantial percentage of an aqueous buffer containing large macromolecules. RNA, DNA and intact virions can be encapsulated within the aqueous interior and delivered to brain cells in a biologically active form (Fraley et al., *Trends Biochem. Sci.*, 1981, 6, 77). The composition of the liposome is usually a combination of lipids, particularly phospholipids, in particular, high phase transition temperature phospholipids, usually in combination with one or more steroids, particularly cholesterol. Examples of lipids useful in liposome production include phosphatidyl compounds, such as phosphatidylglycerol, phosphatidylcholine, phosphatidylserine, phosphatidylethanolamine, sphingolipids, cerebrosides and gangliosides. Particularly useful are diacyl phosphatidylglycerols, where the lipid moiety contains from 14–18 carbon atoms, particularly from 16–18 carbon atoms, and is saturated (lacking double bonds within the 14–18 carbon atom chain). Illustrative phospholipids include phosphatidylcholine, dipalmitoylphosphatidylcholine and distearoylphosphatidylcholine.

The targeting of colloidal dispersion systems, including liposomes, can be either passive or active. Passive targeting utilizes the natural tendency of liposomes to distribute to cells of the reticuloendothelial system in organs that contain sinusoidal capillaries. Active targeting, by contrast, involves modification of the liposome by coupling thereto a specific ligand such as a viral protein coat (Morishita et al., *Proc. Natl. Acad. Sci.* (U.S.A.), 1993, 90, 8474), monoclonal antibody (or a suitable binding portion thereof), sugar, glycolipid or protein (or a suitable oligopeptide fragment thereof), or by changing the composition and/or size of the liposome in order to achieve distribution to organs and cell types other than the naturally occurring sites of localization. The surface of the targeted colloidal dispersion system can be modified in a variety of ways. In the case of a liposomal targeted delivery system, lipid groups can be incorporated into the lipid bilayer of the liposome in order to maintain the targeting ligand in close association with the lipid bilayer. Various linking groups can be used for joining the lipid chains to the targeting ligand. The targeting ligand, which binds a specific cell surface molecule found predominantly on cells to which delivery of the oligonucleotides of the invention is desired, may be, for example, (1) a hormone, growth factor or a suitable oligopeptide fragment thereof which is bound by a specific cellular receptor predominantly expressed by cells to which delivery is desired or (2) a polyclonal or monoclonal antibody, or a suitable fragment thereof (e.g., Fab; F(ab')$_2$) which specifically binds an antigenic epitope found predominantly on targeted cells. Two or more bioactive agents (e.g., an oligonucleotide and a conventional drug; two oligonucleotides) can be combined within, and delivered by, a single liposome. It is also possible to add agents to colloidal dispersion systems which enhance the intercellular stability and/or targeting of the contents thereof.

Compositions for parenteral, intrathecal or intraventricular administration, or colloidal dispersion systems, may include sterile aqueous solutions which may also contain buffers, diluents and other suitable additives. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}s$ found to be effective in in vitro and in vivo animal models. In general, dosage is from 0.01 μg to 100 g per kg of body weight, and may be given once or more daily, weekly, monthly or yearly, or even once every 2 to 20 years.

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

EXAMPLES

Example 1

Chemical Synthesis and Nucleotide Sequence of Oligonucleotides

General Synthetic Techniques

Oligonucleotides were synthesized on an automated DNA synthesizer using standard phosphoramidite chemistry with oxidation using iodine. β-Cyanoethyldiisopropyl phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one-1,1-dioxide in acetonitrile for the stepwise thiation of the phosphite linkages.

The synthesis of 2'-O-methyl- (a.k.a. 2'-methoxy-) phosphorothioate oligonucleotides was according to the procedures set forth above substituting 2'-O-methyl β-cyanoethyldiisopropyl phosphoramidites (Chemgenes, Needham, Mass.) for standard phosphoramidites and increasing the wait cycle after the pulse delivery of tetrazole and base to 360 seconds.

Similarly, 2'-O-propyl- (a.k.a 2'-propoxy-) phosphorothioate oligonucleotides were prepared by slight modifications of this procedure and essentially according to procedures disclosed in U.S. patent application Ser. No. 08/383,666, filed Feb. 3, 1995, which is assigned to the same assignee as the instant application and which is incorporated by reference herein.

The 2'-fluoro-phosphorothioate oligonucleotides of the invention were synthesized using 5'-dimethoxytrityl-3'-phosphoramidites and prepared as disclosed in U.S. patent application Ser. No. 08/383,666, filed Feb. 3, 1995, and U.S. Pat. No. 5,459,255, which issued Oct. 8, 1996, both of which are assigned to the same assignee as the instant application and which are incorporated by reference herein. The 2'-fluoro-oligonucleotides were prepared using phosphoramidite chemistry and a slight modification of the standard DNA synthesis protocol (i.e., deprotection was effected using methanolic ammonia at room temperature).

The 2'-methoxyethoxy oligonucleotides were synthesized essentially according to the methods of Martin et al. (*Helv. Chim. Acta*, 1995, 78, 486). For ease of synthesis, the 3' nucleotide of the 2'-methoxyethoxy oligonucleotides was a deoxynucleotide, and 2'-O—$CH_2CH_2OCH_3$-cytosines were 5-methyl cytosines, which were synthesized according to the procedures described below.

PNA antisense analogs were prepared essentially as described in U.S. Pat. Nos. 5,539,082 and 5,539,083, both of which (1) issued Jul. 23, 1996, (2) are assigned to the same assignee as the instant application and (3) are incorporated by reference herein.

Oligonucleotides comprising 2,6-diaminopurine were prepared essentially as described in U.S. Pat. No. 5,506,351 which issued Apr. 9, 1996, is assigned to the same assignee as the instant application and which is incorporated by reference herein. Oligonucleotides comprising 2,6-diaminopurine can also be prepared by enzymatic means (Bailly et al., *Proc. Natl. Acad. Sci.* U.S.A., 1996, 93:13623).

After cleavage from the controlled pore glass (CPG) column (Applied Biosystems) and deblocking in concentrated ammonium hydroxide, at 55° C. for 18 hours, the oligonucleotides were purified by precipitation 2× from 0.5 M NaCl with 2.5 volumes of ethanol. Analytical gel electrophoresis was accomplished in 20% acrylamide, 8 M urea and 45 mM Tris-borate buffer (pH 7).

Synthesis of 5-Methyl Cytosine Monomers 2,2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a preheated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour.

Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approximately 90% product). The residue was purified on a 3.5 kg silica gel column and eluted using EtOAc/Hexane (4:1). Pure product fractions were evaporated to yield 96 g (84%).

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. Methanol (400 mL) saturated with $NH_3$ gas was added and the vessel heated to 100° C. for 2 hours (thin layer chromatography, tlc, showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

$N^4$-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

$N^4$-Benzoyl-2'-O-methoxyethyl-5'-O-dimethoxytrityl-5-methylcytidine-3'-amidite $N^4$-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc\Hexane (3:1) as the eluting solvent. The pure fractions were combined to give 90.6 g (87%) of the title compound.

Nucleotide Sequences

Table 1 shows the sequence and activity of each of the oligonucleotides evaluated for inhibition of c-jun mRNA expression, and Table 2 shows the sequence and activity of the oligonucleotides evaluated for inhibition of c-fos mRNA expression. Oligonucleotide activities were evaluated as described infra in Example 2 et seq. For the nucleotide sequence of the human c-jun gene, see Hattori et al., *Proc. Natl. Acad. Sci. U.S.A.*, 1988, 85:9148, and Genbank accession No. J04111 ("HUMJUNA"). The nucleotide sequence of the human c-fos gene is described by Van Straaten et al., *Proc. Natl. Acad. Sci. U.S.A.*, 1983, 80:3183, and in Genbank accession No. K00650 ("HUMFOS").

TABLE 1

Phosphorothioate Oligonucleotides Targeted to Human c-jun

| ISIS # | SEQUENCE | SEQ ID NO: | TARGET REGION | % CONTROL* |
|---|---|---|---|---|
| 10570 | GCC-ACA-CTC-AGT-GCA-ACT-CT | 1 | 5' Cap | 62 |
| 10571 | CGC-ACC-TCC-ACT-CCC-GCC-TC | 2 | 5'-UTR | 100 |

TABLE 1-continued

Phosphorothioate Oligonucleotides Targeted to Human c-jun

| ISIS # | SEQUENCE | SEQ ID NO: | TARGET REGION | % CONTROL* |
|---|---|---|---|---|
| 10572 | ACC-AGC-CCG-GGA-GCC-ACA-GG | 3 | 5'-UTR | 39 |
| 10578 | GCT-GCG-CCG-CCG-ACG-TGA-CG | 4 | ORF | 37 |
| 10579 | CGC-CCC-GCC-GCC-GCT-GCT-CA | 5 | ORF | 41 |
| 10580 | GTG-TCT-CGC-CGG-GCA-TCT-CG | 6 | ORF | 19 |
| 10581 | CCC-CCG-ACG-GTC-TCT-CTT-CA | 7 | tTR | 24 |
| 10582 | TCA-GCC-CCC-GAC-GGT-CTC-TC | 8 | 3'--UTR | 17 |
| 10583 | TGC-CCC-TCA-GCC-CCC-GAC-GG | 9 | 3'--UTR | 20 |
| 13305 | TGC-GGG-TGA-GTG-GTA-G | 118 | ORF | N.D. ** |
| 10582 Controls: | | | | |
| 10582 | TCA-GCC-CCC-GAC-GGT-CTC-TC | 8 | 3'--UTR | |
| 11562 | GAG-AGA-CCG-TCG-GGG-GCT-GA | 29 | sense | control |
| 11563 | CAC-CTC-CAC-GCG-CTT-CTG-GC | 30 | scrambled | control |
| 11564 | TCG-GCA-CCT-GAA-GGA-CTT-TC | 31 | mismatch | control |

*Control is TPA induction, at 1 hour, in A549 cells.
** N.D., not determined.

TABLE 2

Phosphorothioate Oligonucleotides Targeted to Human c-fos

| ISIS # | SEQUENCE | SEQ ID NO: | TARGET REGION | % CONTROL* |
|---|---|---|---|---|
| 10628 | TGC-TCG-CTG-CAG-ATG-CGG-TT | 10 | 5' Cap | 79 |
| 10629 | CGG-TCA-CTG-CTC-GTT-CGC-TG | 11 | 5'-UTR | 72 |
| 10630 | CAT-CGT-GGC-GGT-TAG-GCA-AA | 12 | tIR | 91 |
| 10631 | GAG-AAC-ATC-ATC-GTG-GCG-GT | 13 | tIR | 118 |
| 10632 | ACC-GTG-GGA-ATG-AAG-TTG-GC | 14 | ORF | 63 |
| 10633 | AGC-TCC-CTC-CTC-CGG-TTG-CG | 15 | ORF | 24 |
| 10634 | TTG-CAG-GCA-GGT-CGG-TGA-GC | 16 | ORF | 42 |
| 10635 | TGG-CAC-GGA-GCG-GGC-TGT-CT | 17 | ORF | 12 |
| 10636 | TGC-TGC-TGC-CCT-TGC-GGT-GG | 18 | ORF | 42 |
| 10637 | CCT-CAC-AGG-GCC-AGC-AGC-GT | 19 | tTR | 35 |
| 10638 | GGT-GCC-GGC-TGC-CTC-CCC-TT | 20 | 3'-UTR | 22 |
| 10639 | AAG-TCC-TTG-AGG-CCC-ACA-GC | 21 | 3'-UTR | 9 |
| 10640 | CCC-CTC-CAG-CAG-CTA-CCC-TT | 22 | 3'-UTR | 87 |
| 10641 | TCC-CGT-CCC-CAG-AAG-CAG-TA | 23 | 3'-UTR | 68 |
| 10642 | CGC-GCC-CGG-CCT-GAA-AAT-TT | 24 | 3'-UTR | 87 |
| 10643 | CCT-GCC-TCG-GCC-TCC-CAA-AG | 25 | 3'-UTR | 39 |
| 10644 | CCC-CCA-CTT-CCG-CCC-ACT-AT | 26 | 3'-UTR | 104 |
| 10645 | TGG-TGC-CTG-CGT-GAT-ACT-CG | 27 | 3'-UTR | 56 |
| 10646 | CCC-TCC-CAG-GCT-CAA-GTC-AT | 28 | 3'-UTR | 100 |
| 10639 Controls: | | | | |
| 10639 | AAG-TCC-TTG-AGG-CCC-ACA-GC | 21 | 3'-UTR | |
| 11184 | GCT-GTG-GGC-CTC-AAG-GAC-TT | 32 | sense | control |
| 11185 | ATG-TGC-TAG-ATG-CGC-AAA-GT | 33 | mismatch | control |
| 11186 | ACG-TCC-GAT-TCC-GAG-CGC-AA | 34 | scrambled | control |
| 11187 | CAG-TGG-CCA-TCA-AAC-CCG-TG | 35 | scrambled | control |

*Control is TPA induction, at 1 hour, in A549 cells.

Example 2

Screening for Oligonucleotides that Modulate mRNA Expression of the AP-1 Subunits c-fos and c-jun In order to evaluate the activity of potential c-fos and c-jun modulating oligonucleotides, A549 cells were grown in T-75 flasks until 80–90% confluent. (Cell line A549 is available from, inter alia, the American Type Culture Collection, Rockville, Md., as ATCC No. CCL-185.) At this time, the cells were washed twice with 10 mL of media (DMEM), followed by the addition of 5 mL of DMEM containing 20 µg/mL of LIPOFECTIN™ (i.e., DOTMA/ DOPE (N-[1-(2,3-dioleyloxy)propyl]-N,N,N-triethylammonium chloride/dioleoylphosphatidyl ethanolamine)). The oligonucleotides were added from a 10 µM stock solution to a final concentration of 400 nM, and the two solutions were mixed by swirling the flasks. After 4 hours at 37° C., the medium was replaced with DMEM containing 10% serum. At this point, 1 µM 12—O—tetradecanoylphorbol 13-acetate (TPA) was added to induce expression of c-fos and c-jun. Cells were extracted in guanidinium one hour later, and the c-fos and c-jun mRNA expression was determined by Northern blotting. Probes for human c-jun and c-fos were PCR products prepared using primers based on the published sequences thereof (respectively, Hattori et al., Proc. Natl. Acad. Sci. U.S.A., 1988, 85:9148, and Van Straaten et al., Proc. Natl. Acad. Sci. U.S.A., 1983, 80:3183).

As described in Table 1, for inhibiting c-jun mRNA expression, ISIS 10580, 10581, 10582 and 10583 were most active (81%, 76%, 83% and 80% inhibition, respectively). Treatment of cells with these oligonucleotides reduced c-jun expression to 19%, 24%, 17% and 20% (81%, 76%, 83% and 80% inhibition), respectively, of the level seen in control experiments (100% expression, 0% inhibition). These oligonucleotides effect significant inhibition of c-jun and are therefor preferred. Basal levels of c-jun mRNA are typically about 30% of the control value; ISIS 10572, 10578 and 10579 reduce c-jun levels to near basal levels (39%, 37% and 41%, respectively) and are thus also preferred.

As described in Table 2, the oligonucleotides most effective in reducing c-fos mRNA expression are ISIS 10633, 10635, 10638 and 10639. Treatment of cells with these oligonucleotides reduced c-fos expression to 24%, 12%, 22% and 9% (76%, 88%, 78% and 91% inhibition), respectively, of the level seen in control experiments (100% expression, 0% inhibition); basal levels of c-fos mRNA are typically about 3% of the control value. These oligonucleotides effect significant inhibition of c-fos and are therefor preferred.

Example 3

Dose Response and Specificity of Oligonucleotides Targeted to AP-1 Subunits

Dose-response experiments were performed at different oligonucleotide concentrations to determine the potency (i.e., ability to decrease expression of the appropriate mRNA target) of the most active compounds identified in the initial screen (Tables 3 and 4). The decreases in target mRNA expression effected by ISIS 10582 (c-jun) and ISIS 10639 (c-fos) are dose-dependent, as shown in Tables 3 and 4, respectively.

TABLE 3

Dose-Response to Oligonucleotides Targeted to c-jun

| TREATMENT | OLIGONUCLEOTIDE CONCENTRATION | c-jun mRNA LEVELS (% CONTROL) |
|---|---|---|
| None (basal level) | — | 31 |
| Control* | — | 100 |
| TPA + ISIS 10582 | 50 nM | 72 |
| TPA + ISIS 10582 | 100 nM | 45.5 |
| TPA + ISIS 10582 | 200 nM | 29.5 |
| TPA + ISIS 10582 | 400 nM | 16 |

*Control is TPA induction, at 1 hour, in A549 cells.

TABLE 4

Dose-Response to Oligonucleotides Targeted to c-fos

| TREATMENT | OLIGONUCLEOTIDE CONCENTRATION | c-fos mRNA LEVELS (% CONTROL) |
|---|---|---|
| None (basal level) | — | 3 |
| Control* | — | 100 |
| TPA + ISIS 10639 | 50 nM | 64 |
| TPA + ISIS 10639 | 100 nM | 46 |
| TPA + ISIS 10639 | 200 nM | 20.5 |
| TPA + ISIS 10639 | 400 nM | 9 |

*Control is TPA induction, at 1 hour, in A549 cells.

The specificity of the oligonucleotide-mediated inhibition of c-fos and c-jun mRNA expression was further examined by determining the effects of scrambled, 6- or 7-base mismatch and sense control versions of the most active oligonucleotides, ISIS 10582 (c-jun) and ISIS 10639 (c-fos). As can be seen in Table 5, ISIS 10582 exhibited potent and specific inhibition of c-jun mRNA expression, but ISIS 11562 (sense version of ISIS 10582; SEQ ID NO:29), ISIS 11564 (6 base pair mismatch version of ISIS 10639; SEQ ID NO:31) and ISIS 11563 (scrambled version of ISIS 10639; SEQ ID NO:30) had no detectable effect on c-jun mRNA levels during TPA induction (the sequences of ISIS 11562–11564 are given in Table 1).

As can further be seen in Table 5, ISIS 10639 exhibited potent and specific inhibition of c-fos mRNA expression, but ISIS 11184 (sense version of ISIS 10639; SEQ ID NO:32), ISIS 11185 (7 base pair mismatch version of ISIS 10639; SEQ ID NO:33) and ISIS 11186 (scrambled version of ISIS 10639; SEQ ID NO:34) had no detectable effect on c-fos mRNA levels during TPA induction (the sequences of ISIS 11184–11186 are given in Table 2). Finally, it can also be seen from Table 5 that neither active oligonucleotide has any detectable effect on mRNA levels of the other active oligonucleotide's target. That is, ISIS 10639, targeted to c-fos, has no detectable effect on c-jun levels; similarly, ISIS 10582, targeted to c-jun, has no detectable effect on c-fos levels.

TABLE 5

Specificity of c-fos and c-jun Oligonucleotides

| Treatment | c-fos | c-jun |
|---|---|---|
| Basal | 5 | 23 |
| TPA-no oligo | 100 | 100 |
| 10639: c-fos active | 9 | 97 |
| 11184: c-fos sense | 84 | 91 |
| 11185: c-fos mismatch | 93 | 98 |
| 11186: c-fos scrambled | 98 | 99 |
| 10582: c-jun active | 91 | 4 |
| 11562: c-jun sense | 89 | 87 |
| 11563: c-jun scrambled | 99 | 93 |
| 11564: c-jun mismatch | 99 | 71 |

These results demonstrate that ISIS 10582 effects potent and specific modulation (i.e., inhibition) of c-jun mRNA levels and that ISIS 10639 effects potent and specific modulation of c-fos mRNA levels.

Example 4

Effect of Oligonucleotides Targeted to an AP-1 Subunit on Human Tumor Growth in Nude Mice In order to evaluate the in vivo activity of c-fos oligonucleotides, 25 mg of tumor fragments of A549 tumors were implanted subcutaneously in nude mice (n=6). ISIS 10639 was administered daily, i.v., for three weeks. The oligonucleotide dosage was 25 mg/kg. Tumor size was recorded weekly, and the results are shown in Table 6. A substantial reduction in tumor growth rate was obtained upon treatment with ISIS 10639. By day 34, saline-treated tumors were 0.56±0.12 g by weight, while tumors treated with ISIS 10639 were 0.31±0.1 g by weight.

TABLE 6

Response of Transplanted Tumors in Mice to Oligonucleotides Targeted to c-jun

| Treatment/Time | Mean Tumor Weight (g) | Std. Dev. | Std. Error |
|---|---|---|---|
| Saline: | | | |
| Day 17 | 0.113 | 0.033 | 0.014 |
| Day 20 | 0.177 | 0.045 | 0.019 |
| Day 27 | 0.272 | 0.086 | 0.035 |
| Day 34 | 0.560 | 0.293 | 0.120 |
| ISIS 10639: | | | |
| Day 17 | 0.105 | 0.035 | 0.014 |
| Day 20 | 0.138 | 0.074 | 0.030 |
| Day 27 | 0.225 | 0.070 | 0.028 |
| Day 34 | 0.310 | 0.104 | 0.042 |

TABLE 7

Effect of c-fos Oligonucleotides on c-Fos Protein Levels

| Treatment | c-Fos |
|---|---|
| Basal | 21 |
| TPA-no oligo | 100 |
| 10639: c-fos active | 19 |
| 11184: c-fos sense | 97 |
| 11185: c-fos mismatch | 91 |
| 11186: c-fos scrambled | 99 |

Example 5

Effect of Oligonucleotides on Protein Levels of AP-1 Subunits

The ability of the c-fos active oligonucleotide ISIS 10639 to reduce expression of the c-Fos protein was examined as follows. A549 cells were treated with oligonucleotides as in Examples 2–3, except that induction of c-Fos was effected by treatment of cells with TPA (1 uM) for three hours. At this time, whole cell protein was extracted in SDS (sodium dodecyl sulfate) buffer. Samples of extracts were electrophoresed, transferred to nitrocellulose filters which were immunoblotted using a c-Fos-specific antibody (Santa Cruz AB, Santa Cruz, Calif.). The results (Table 7) demonstrate that treatment of cells with the c-fos antisense oligonucleotide results in basal levels of c-Fos protein.

Example 6

Modified Oligonucleotides and PNA Antisense Analogs to Human AP-1 Subunits

Once oligonucleotides that modulate c-Fos or c-Jun are identified, derivative or modified oligonucleotides having the same sequence thereas are prepared. In order to evaluate the effect of chemical modifications to oligonucleotides to c-fos and c-jun, the modified oligonucleotides described in Tables 8 and 9 were prepared. The effect of the c-fos-targeted oligonucleotides on c-fos RNA levels were evaluated as described in Examples 2–3. The results (Table 10) demonstrate that some enhancement of c-fos modulation can be achieved by the use modifications such as, e.g., 2'-fluoro (ISIS 11200). Other modified oligonucleotides of the invention are evaluated in like fashion. In order to evaluate the effect of PNA antisense analogs, the PNA analogs of the invention are introduced into appropriate cell lines by microinjection according to the method of Hanvey et al. (*Science,* 1992, 258:1481). Intracellular delivery of PNA analogs is confirmed by the use of a fluorescently tagged PNA antisense analog conjugate such as, e.g., ISIS 14240.

TABLE 8

Additional Oligonucleotides and PNA Antisense Analogs Targeted to Human AP-1 Subunits

| ISIS # | Target | Oligonucleotide Sequence (5' -> 3') and Chemical Modifications* | SEQ ID NO: |
|---|---|---|---|
| C-JUN: | | | |
| 10570 & | Derivatives: | | |
| 10570 | c-jun, 5' cap | $G^SC^SC^SA^SC^SA^SC^ST^SC^SA^SG^ST^SG^SC^SA^SA^SC^ST^SC^ST$ P=S | 1 |
| 13306 | c-jun, 5' cap | $C^SA^SC^ST^SC^SA^SG^ST^SG^SC^SA^SA^SC^ST^SC^ST$ P=S | 36 |
| 13297 | c-jun, 5' cap | $C^SA^SC^ST^SC^SA^SG^ST^SG^SC^SA^SA^SC^ST^SC^ST$ P=S/2'MO | 36 |
| 12166 | c-jun, 5' cap | $C^NA^NC^NT^NC^NA^NG^NT^NG^NC^NA^NA^NC^NT^NC^NT^N$ PNA(N) | 36 |
| 13699 | c-jun, 5' cap | $C^NA^NC^NT^KC^NA^NG^NT^KG^NC^NA^NA^NC^NT^KC^NT^K$ PNA(N) /Lys(K) | 36 |
| 10579 & | Derivatives: | | |
| 10579 | c-jun, ORF | $C^SG^SC^SC^SC^SC^SG^SC^SC^SG^SC^SC^SG^SC^ST^SG^SC^ST^SC^SA$ P=S | 5 |
| 11567 | c-jun, ORF | $C^SG^SC^SC^SC^SC^SG^SC^SC^SG^SC^SC^SG^SC^ST^SG^SC^ST^SC^SA$ 2'F | 5 |
| 10571 & | Derivatives: | | |
| 10571 | c-jun, 5'-UTR | $C^SG^SC^SA^SC^SC^ST^SC^SC^SA^SC^ST^SC^SC^SC^SG^SC^SC^ST^SC$ P=S | 2 |
| 11568 | c-jun, 5'-UTR | $C^SG^SC^SA^SC^SC^ST^SC^SC^SA^SC^ST^SC^SC^SC^SG^SC^SC^ST^SC$ 2'F | 2 |
| 13307 | c-jun, 5'-UTR | $C^SC^ST^SC^SC^SA^SC^ST^SC^SC^SC^SG^SC^SC^ST^SC$ P=S | 37 |
| 13296 | c-jun, 5'-UTR | $C^SC^ST^SC^SC^SA^SC^ST^SC^SC^SC^SG^SC^SC^ST^SC$ P=S/2'MO | 37 |
| 12167 | c-jun, 5'-UTR | $C^NC^NT^NC^NC^NA^NC^NT^NC^NC^NC^NG^NC^NC^NT^NC^N$ PNA(N) | 37 |
| 13698 | c-jun, 5'-UTR | $C^NC^NT^KC^NC^NA^NC^NT^KC^NC^NC^NG^NC^NC^NT^KC^N$ PNA(N) /Lys(K) | 37 |
| 10582 & | Derivatives: | | |
| 10582 | c-jun, 3'-UTR | $T^SC^SA^SG^SC^SC^SC^SC^SG^SA^SC^SG^SG^ST^SC^ST^SC^ST^SC$ P=S | 8 |
| 11569 | c-jun, 3'-UTR | $T^SC^SA^SG^SC^SC^SC^SC^SG^SA^SC^SG^SG^ST^SC^ST^SC^ST^SC$ 2'F | 8 |
| 11537 | c-jun, 3'-UTR | $T^SC^SA^SG^SC^SC^SC^SC^SG^SA^SC^SG^SG^ST^SC^ST^SC^ST^SC$ 2'propoxy- | 8 |
| 14314 | c-jun, 3'-UTR | $T^SC^SA^SG^SC^SC^SC^SC^SG^SA^SC^SG^SG^ST^SC^ST^SC^ST^SC$ 2'ME | 8 |

TABLE 8-continued

Additional Oligonucleotides and PNA Antisense Analogs Targeted to Human AP-1 Subunits

| ISIS # | Target | Oligonucleotide Sequence (5' -> 3') and Chemical Modifications* | SEQ ID NO: |
|---|---|---|---|
| C-FOS: | | | |
| 10639 & | Derivatives: | | |
| 10639 | c-fos, 3'-UTR | $A^SA^SG^ST^SC^SC^ST^ST^SG^SA^SG^SG^SC^SC^SC^SA^SC^SA^SG^SC$ P=S | 21 |
| 11200 | c-fos, 3'-UTR | $A^SA^SG^ST^SC^SC^ST^ST^SG^SA^SG^SG^SC^SC^SC^SA^SC^SA^SG^SC$ 2'MO | 21 |
| 11538 | c-fos, 3'-UTR | $A^SA^SG^ST^SC^SC^ST^ST^SG^SA^SG^SG^SC^SC^SC^SA^SC^SA^SG^SC$ 2'propoxy- | 21 |
| 14315 | c-fos, 3'-UTR | $A^SA^SG^ST^SC^SC^ST^ST^SG^SA^SG^SG^SC^SC^SC^SA^SC^SA^SG^SC$ 2'ME | 21 |
| 13298 & | Derivatives: | | |
| 13298 | c-fos, ORF | $T^SG^SC^SG^SG^SG^ST^SG^SA^SG^ST^SG^SG^ST^SA^SG$ 2'ME | 120 |
| 12165 | c-fos, ORF | $T^NG^NC^NG^NG^NG^NT^NG^NA^NG^NT^NG^NG^NT^NA^NG^N$ PNA(N) | 120 |
| 13646 | c-fos, ORF | $T^NG^NC^NG^NG^NG^NT^KG^NA^NG^NT^KG^NG^NT^KA^NG^N$ PNA(N)/Lys(K) | 120 |
| 10628 & | Derivatives: | | |
| 10628 | c-fos, 5' cap | $T^SG^SC^ST^SC^SG^SC^ST^SG^SC^SA^SG^SA^ST^SG^SC^SG^SG^ST^ST$ P=S | 10 |
| 13302 | c-fos, 5' cap | $C^SG^SC^ST^SG^SC^SA^SG^SA^ST^SG^SC^SG^SG^ST^ST$ P=S | 121 |
| 13301 | c-fos, 5' cap | $C^SG^SC^ST^SG^SC^SA^SG^SA^ST^SG^SC^SG^SG^ST^ST$ P=S, 2'MO | 121 |
| 12162 | c-fos, 5' cap | $C^NG^NC^NT^NG^NC^NA^NG^NA^NT^NG^NC^NG^NG^NT^NT$ PNA(N) | 121 |
| 13643 | c-fos, 5' cap | $C^NG^NC^NT^KG^NC^NA^NG^NA^NT^KG^NC^NG^NG^NT^KT$ PNA(N) /Lys(K) | 121 |
| 13303 & | Derivatives: | | |
| 13303 | c-fos, 5'-UTR | $C^SC^SG^SC^SC^SG^SG^SC^ST^SC^SA^SG^ST^SC^ST^ST$ P=S | 122 |
| 13300 | c-fos, 5'-UTR | $C^SC^SG^SC^SC^SG^SG^SC^ST^SC^SA^SG^ST^SC^ST^ST$ P=S, 2'MO | 122 |
| 12163 | c-fos, 5'-UTR | $C^NC^NG^NC^NC^NG^NG^NC^NT^NC^NA^NG^NT^NC^NT^NT^N$ PNA(N) | 122 |
| 13644 | c-fos, 5'-UTR | $C^NC^NG^NC^NC^NG^NG^NC^NT^KC^NA^NG^NT^KC^NT^KT^{K\ PNA(N)/Lys(K)}$ | 122 |
| 13304 & | Derivatives: | | |
| 13304 | c-fos, tIR | $C^SA^ST^SC^SG^ST^SG^SG^SC^SG^SG^ST^ST^SA^SG^SG$ P=S | 123 |
| 13299 | c-fos, tIR | $C^SA^ST^SC^SG^ST^SG^SG^SC^SG^SG^ST^ST^SA^SG^SG$ P=S, 2'MO | 123 |
| 12164 | c-fos, tIR | $C^NA^NT^NC^NG^NT^NG^NG^NC^NG^NG^NT^NT^NA^NG^NG^N$ PNA(N) | 123 |
| 13700 | c-fos, tIR | $C^KA^NT^KC^KG^NT^KG^NG^NC^KG^NG^NT^KT^KA^NG^NG^{K\ PNA(N)/Lys(K)}$ | 123 |
| 14240 | c-fos, tIR | $C^KA^NT^KC^KG^NT^KG^NG^NC^KG^NG^NT^KT^KA^NG^NG^{K\ PNA(N)}$ /Lys(K)/5'FITC | 123 |

*Phosphorothioate linkages are indicated by "S" and "P=S"; emboldened residues indicate the additional indicated modifications:
2'F = 2'-fluoro-;
2'propoxy =2'-propoxy-;
2'MO = 2'-methoxy-;
2'ME = 2'-methoxyethoxy-;
PNA = peptide (polyamide) nucleic acid backbone having a side chain corresponding to that of either glycine (N) or D-Lys (K);
5'FITC = 5'-fluorescein isothiocyanate.

TABLE 9

5-Methyl-Cytosine, Fully 2'-Methoxyethoxy-Oligonucleotides
Targeted to the 3'-UTR of Human c-fos

| ISIS NO. | SEQUENCE | SEQ ID NO. |
|---|---|---|
| 15828 | $C^OC^OA^OT^OC^OT^OT^OA^OA^OT^OA^OA^OA^OT^OA^OA^OA^OT^OT^OA^OA^OA^OA^OA^OC^OA^OC^OA^OA^OT$ | 131 |
| 14660 | $A^OA^OA^OT^OA^OA^OA^OT^OT^OA^OA^OA^OA^OA^OC^OA^OC^OA^OA^OT$ 2,6-A* | 132 |
| 14659 | $A^OA^OT^OT^OA^OA^OA^OA^OA^OC^OA^OC^OA^OA^OT^OA^OA^OA^OA^OC$ 2,6-A | 133 |
| 15829 | $A^OT^OA^OT^OA^OA^OA^OT^OA^OT^OC^OT^OG^OA^OG^OA^OA^OT^OC^OC$ | 134 |
| 14662 | $A^OT^OA^OT^OA^OA^OA^OT^OA^OT^OC^OT^OG^OA^OG^OA^OA^OT^OC^OC$ 2,6-A | 135 |
| 14661 | $A^OT^OC^OT^OG^OA^OG^OA^OA^OT^OC^OC^OA^OT^OC^OT^OT^OA^OA^OT$ 2,6-A | 136 |
| 14663** | $A^OA^OA^OT^OA^OT^OA^OA^OA^OT^OA^OT^OC^OT^OG^OA^OG^OA^OA^OT$ 2,6-A | 137 |
| 14664 | $A^OA^OG^OA^OC^OC^OT^OC^OA^OA^OG^OG^OT^OA^OG^OA^OA^OA^OA$ | 138 |

*Emboldened residues indicate 2,6-A residues, i.e., those having 2,6-diaminopurine as a nucleobase.
**ISIS 14663 is a 2'-deoxy- rather than a 2'-methoxyethoxy-oligonucleotide.

TABLE 10

Effect of Modified c-fos Oligonucleotides on c-fos Expression

| Treatment | c-fos |
| --- | --- |
| Basal | 3 |
| TPA-no oligo | 100 |
| 10639: c-fos active, P=S | 9 |
| 11200: c-fos, 2'-fluoro- | 5 |
| 11538: c-fos, 2'-propoxy- | 15 |

Example 7

Oligonucleotides to Mouse AP-1 Subunits

Tables 11 and 12 show the sequences of oligonucleotides designed to modulate mouse c-jun and c-fos mRNA expression, respectively. For the nucleotide sequence of the mouse c-jun gene, see Genbank accession No. J04115/MUSCJUN and Ryder et al., *Proc. Natl. Acad. Sci. U.S.A.*, 1988, 85:8464. The nucleotide sequence of the mouse c-fos gene is described in Genbank accession No. J00370/MUSFOS and by Van Beveren et al., *Cell*, 1983, 32:1241. Oligonucleotide activities are evaluated as described infra in Example 2 et seq. with the exception that mouse Swiss 3T3 cells (available from, inter alia, the American Type Culture Collection, Rockville, Md., as ATCC No. CCL-92) are used instead of human A549 cells. Due to the high degree of homology between human and murine c-jun and c-fos nucleotide sequences (Van Straaten et al., *Proc. Natl. Acad. Sci. U.S.A.*, 1983, 80:3183), probes derived from the human genes were used to detect murine messages.

TABLE 11

Phosphorothioate Oligonucleotides Targeted to Mouse c-jun

| ISIS # | SEQUENCE | SEQ ID NO: | TARGET REGION* |
| --- | --- | --- | --- |
| 12292 | CTC-GCC-CAA-CTT-CAG-CCG-CC | 38 | 5'-UTR: 434–453 |
| 12293 | CCA-GTC-CCA-GCA-ACA-GCG-GC | 39 | 5'-UTR: 588–607 |
| 12294 | GCA-ACA-GCG-CGC-CGG-GAA-GC | 40 | 5'-UTR: 838–857 |
| 12295 | CCG-GCG-ACG-CCA-GCT-TGA-GC | 41 | ORF: 1120–1139 |
| 12296 | GGC-TGT-GCC-GCG-GAG-GTG-AC | 42 | ORF: 1304–1323 |
| 12297 | CGC-CCC-ACC-GCC-GCT-GCT-CA | 43 | ORF: 1458–1477 |
| 12298 | AGC-CCG-GCC-GCG-CCA-TAG-GA | 44 | ORF: 1481–1500 |
| 12299 | CTG-CAC-CGG-GAT-CTG-TTG-GG | 45 | ORF: 1560–1579 |
| 12300 | GGC-GGC-GTC-TCT-CCC-GGC-ATC-TC | 46 | ORF: 1625–1647 |
| 12301 | TGG-AGG-CGG-CAA-TGC-GGT-TC | 47 | ORF: 1708–1727 |
| 12302 | CCC-TGA-GCA-TGT-TGG-CCG-TG | 48 | ORF: 1813–1832 |
| 12303 | CAA-AGC-CAG-GCG-CGC-CAC-GT | 49 | 3'-UTR: 2096–2115 |
| 12304 | TTG-AGA-GAG-GCA-GGC-CAG-GG | 50 | 3'-UTR: 2388–2407 |
| 12305 | TGG-ACT-TGT-GTG-TTG-CCG-GG | 51 | 3'-UTR: 2807–2826 |
| 12306 | TCC-ATG-GGT-CCC-TGC-TTT-GA | 52 | 3'-UTR: 2999–3018 |
| 12321 | TGG-TCG-CGC-GCG-GGC-ACA-GC | 53 | 3'-UTR: 2166–2185 |

*Nucleotide co-ordinates from Genbank accession No. J04115/MUSCJUN.

TABLE 12

Phosphorothioate Oligonucleotides Targeted to Mouse c-fos

| ISIS # | SEQUENCE | SEQ ID NO: | TARGET REGION* |
| --- | --- | --- | --- |
| 11249 | AGC-TCC-CTC-CTC-CGA-TTC-CG | 54 | ORF: 1905–1924 |
| 11250 | GCT-CTG-TGA-CCA-TGG-GCC-CC | 55 | ORF: 2498–2517 |
| 12307 | GAA-CCG-CCG-GCT-CTA-TCC-AG | 56 | 5'-UTR: 164–183 |
| 12308 | GCC-CCT-GCG-AGT-CAC-ACC-CC | 57 | ORF: 485–504 |
| 12309 | TAA-GGC-TGC-TCT-GAC-CGC-GC | 58 | ORF: 541–560 |
| 12310 | CGC-CCG-CAG-CAC-CCT-CCT-CC | 59 | ORF: 804–823 |
| 12311 | CAG-GCG-CTG-CTC-CGG-AGT-CT | 60 | ORF: 868–887 |
| 12312 | TCC-CTT-GAA-TTC-CGC-AGC-GC | 61 | ORF: 989–1008 |
| 12313 | AGC-GGA-GGT-GAG-CGA-GGA-GG | 62 | ORF: 1136–1155 |
| 12314 | CCC-CAG-CCC-ACA-AAG-GTC-CA | 63 | ORF: 1445–1464 |
| 12315 | TGC-TCA-AGG-ACC-CTG-CGC-CC | 64 | ORF: 2001–2020 |
| 12316 | GGG-AAG-CCA-AGG-TCA-TCG-GG | 65 | ORF: 2178–2197 |
| 12317 | TGC-TGC-TGC-CCT-TTC-GGT-GG | 66 | ORF: 2630–2649 |
| 12318 | CTG-GAT-GCC-GGC-TGC-CTT-GC | 67 | 3'-UTR: 2716–2735 |
| 12319 | CAG-CTC-GGG-CAG-TGG-CAC-GT | 68 | 3'-UTR: 2736–2755 |
| 12320 | GGA-ACA-CGC-TAT-TGC-CAG-GA | 69 | 3'-UTR: 3138–3157 |

*Nucleotide co-ordinates from Genbank accession No. J00370/MUSFOS.

Example 8

Oligonucleotides to Rat AP-1 Subunits

Tables 13 and 14 show the sequences of oligonucleotides designed to modulate rat c-jun and c-fos mRNA expression, respectively. For the nucleotide sequence of the rat c-jun gene, see Genbank accession No. X17163/RSJUNAP1 and Saaki et al., *Cancer Res.,* 1989, 49:5633. The nucleotide sequence of the rat c-fos gene is described in Genbank accession No. X06769/RNCFOSR and Curran et al., *Oncogene,* 1987, 2:79. Oligonucleotide activities were evaluated as described infra in Example 2 et seq. with the exception that rat A10 cells (available from, inter alia, the American Type Culture Collection, Rockville, Md., as ATCC No. CRL-1476) were used instead of human A549 cells. Due to the high degree of homology between human and rat c-jun and c-fos nucleotide sequences, probes derived from the human genes were used to detect the rat messages.

ISIS 12633 (SEQ ID NO:78), a 20-mer phosphorothioate oligonucleotide complementary to a portion of the 3' UTR of rat c-jun mRNA, was selected as an active modulator of c-jun for further studies. Another preferred oligonucleotide targeted to rat AP-1 subunits is ISIS 12635 (SEQ ID NO:80).

Example 9

Modified Oligonucleotides to Rat AP-1 Subunits

Tables 15 and 16 show the sequences and chemical modifications of second generation oligonucleotides designed to modulate mouse c-jun and c-fos mRNA expression. The activities of these modified oligonucleotide are evaluated as described infra in Example 8.

TABLE 13

Phosphorothioate Oligonucleotides Targeted to Rat c-jun

| ISIS # | SEQUENCE | SEQ ID NO: | TARGET REGION* |
|---|---|---|---|
| 12624 | CGG-CGG-CGC-AGA-CCA-GTC-GT | 70 | 5'-UTR: 2–21 |
| 12625 | GCC-GCG-GGA-CCA-GCC-CCA-GC | 119 | 5'-UTR: 35–54 |
| 12626 | GGC-ATC-GTC-GTA-GAA-GGT-CG | 71 | 5'-UTR: 20–39 |
| 12627 | GGA-GGT-GCG-GCT-TCA-GAT-TG | 72 | ORF: 493–512 |
| 12628 | CCC-TCC-TGC-TCG-TCG-GTC-AC | 73 | 5'-UTR: 307–326 |
| 12629 | ACT-GAC-TGG-TTG-TGC-CGC-GG | 74 | ORF: 747–766 |
| 12630 | CGC-TGT-AGC-CGC-CGC-CGC-CG | 75 | ORF: 814–833 |
| 12631 | CCT-TGA-TCC-GCT-CCT-GAG-AC | 76 | ORF: 1105–1124 |
| 12632 | GCC-AGC-TCG-GAG-TTT-TGC-GC | 77 | ORF: 1226–1245 |
| 12633 | TTT-TCT-TCC-ACT-GCC-CCT-CA | 78 | 3'-UTR: 1375–1394 |
| 12634 | CCC-TTG-GCT-TCA-GTA-CTC-GG | 79 | 3'-UTR: 1451–1470 |
| 12635 | CTT-CCC-ACT-CCA-GCA-CAT-TG | 80 | 3'-UTR: 1509–1528 |
| 12636 | GCA-CAG-CCC-GTT-CGC-AAA-GC | 81 | 3'-UTR: 1584–1603 |
| 12637 | AAT-GCA-GCA-GAG-AGG-TTG-GG | 82 | 3'-UTR: 2089–2108 |
| 12638 | GAC-GGG-AGG-GAC-TAC-AGG-CT | 83 | 3'-UTR: 2168–2187 |
| 12639 | TCT-GGA-CTT-GTG-GGT-TGC-TG | 84 | 3'-UTR: 2240–2259 |
| 12640 | TAA-ACG-ATC-ACA-GCG-CAT-GC | 85 | 3'-UTR: 2375–2394 |
| 12628 control: | | | |
| 12628 | CCC-TCC-TGC-TCG-TCG-GTC-AC | 73 | 5'-UTR |
| 12893 | GGG-AGG-ACG-AGC-AGC-CAG-TG | 86 | reverse sense control |
| 12894 | CCC-GGC-CTT-TTG-ACC-GCC-TC | 87 | scrambled control |
| 12895 | CCG-CCT-CCC-CGG-CCT-TTT-GA | 88 | scrambled control |
| 12896 | CCG-TCG-TGG-TCC-TCC-GTG-AC | 89 | mismatch control |
| 12992 | GTG-ACC-GAC-GAG-CAG-GAG-GG | 90 | sense control |
| 12633 control: | | | |
| 12633 | TTT-TCT-TCC-ACT-GCC-CCT-CA | 78 | 3'-UTR |
| 12897 | AAA-AGA-AGG-TGA-CGG-GGA-GT | 91 | reverse sense control |
| 12898 | TTC-TCT-TTT-AGC-CTC-CCC-CA | 92 | scrambled control |
| 12899 | TCC-CCC-ATT-CTC-TTT-TAG-CC | 93 | scrambled control |
| 12900 | TTA-TCA-TCG-ACA-GCG-CCA-CA | 94 | mismatch control |
| 12993 | TGA-GGG-GCA-GTG-GAA-GAA-AA | 95 | sense control |

*Nucleotide co-ordinates from Genbank accession No. X17163/RSJUNAP1.

TABLE 14

Phosphorothioate Oligonucleotides Targeted to Rat c-fos

| ISIS # | SEQUENCE | SEQ ID NO: | TARGET REGION* |
|---|---|---|---|
| 11124 | GTT-CTC-GGC-TCC-GCC-GGC-TC | 96 | 5'-UTR: 22–41 |
| 11245 | CAT-CAT-GGT-CGT-GGT-TTG-GG | 97 | tIR: 122–140 |
| 12246 | TCC-GCG-TTG-AAA-CCC-GAG-AA | 98 | ORF: 141–160 |
| 12247 | TGG-GCT-GGT-GGA-GAT-GGC-TG | 99 | ORF: 328–347 |
| 12248 | CGA-TGC-TCT-GCG-CTC-TGC-CG | 100 | ORF: 485–504 |
| 12251 | TTC-GGT-GGG-CAG-CTG-CGC-AG | 101 | ORF: 1193–1212 |
| 12252 | CAG-GGC-TAG-CAG-TGT-GGG-CG | 102 | tTR: 1255–1274 |
| 12253 | CCA-GCT-CAG-TCA-GTG-CCG-GC | 103 | 3'-UTR: 1299–1318 |
| 12254 | TCT-ACG-GGA-ACC-CCT-CGA-GG | 104 | 3'-UTR: 1348–1367 |
| 12255 | CTC-CAT-GCG-GTT-GCT-TTT-GA | 105 | 3'-UTR: 1518–1537 |
| 12256 | CAG-GCC-TGG-CTC-ACA-TGC-TA | 106 | 3'-UTR: 1576–1595 |

TABLE 14-continued

Phosphorothioate Oligonucleotides Targeted to Rat c-fos

| ISIS # | SEQUENCE | SEQ ID NO: | TARGET REGION* |
|---|---|---|---|
| | 11254 controls: | | |
| 11254 | TCT-ACG-GGA-ACC-CCT-CGA-GG | 104 | 3'-UTR |
| 12698 | AGA-TGC-CCT-TGG-GGA-GCT-CC | 107 | reverse sense control |
| 12699 | TGA-CTA-TAG-ACC-GCC-GCC-GG | 108 | scrambled control |
| 12700 | CCG-CCG-GTG-ACT-ATA-GAC-CG | 109 | scrambled control |
| 12728 | TCA-ACC-GGT-ACG-CCA-CGT-GG | 110 | mismatch control |
| 12990 | CCT-CGA-GGG-GTT-CCC-GTA-GA | 111 | sense control |
| | 11256 controls: | | |
| 11256 | CAG-GCC-TGG-CTC-ACA-TGC-TA | 106 | |
| 12701 | GTC-CGG-ACC-GAG-TGT-ACG-AT | 112 | reverse sense control |
| 12702 | GCG-CAC-CGT-CAT-TAC-GTC-GA | 113 | scrambled control |
| 12703 | ACG-TCG-AGC-GCA-CCG-TCA-TT | 114 | scrambled control |
| 12729 | CAC-GCG-TGC-CTG-ACT-TGG-TA | 115 | mismatch control |
| 12991 | TAG-CAT-GTG-AGC-CAG-GCC-TG | 116 | sense control |

*Nucleotide co-ordinates from Genbank accession No. X06769/RNCFOSR (see also Curran et al., Oncogene, 1987, 2:79).

TABLE 15

Additional Oligonucleotides Targeted to Rat c-jun

| ISIS # | Target | Oligonucleotide Sequence (5' -> 3') and Chemical Modifications* | SEQ ID NO: |
|---|---|---|---|
| 12633 & | Derivatives: | | |
| 12633 | 3'-UTR | T$^S$T$^S$T$^S$T$^S$C$^S$T$^S$T$^S$C$^S$C$^S$A$^S$C$^S$T$^S$G$^S$C$^S$C$^S$C$^S$T$^S$C$^S$A | 78 |
| 13047 | 3'-UTR | T$^O$T$^O$T$^O$T$^O$C$^O$T$^S$C$^S$C$^S$A$^S$C$^S$T$^S$G$^S$C$^S$C$^O$C$^O$C$^O$T$^O$C$^O$A$^d$ 2'MO | 78 |
| 13714 | 3'-UTR | T$^O$T$^O$T$^O$T$^O$C$^O$T$^S$C$^S$C$^S$A$^S$C$^S$T$^S$G$^S$C$^S$C$^O$C$^O$C$^O$T$^O$C$^O$A$^d$ 2'ME | 78 |
| 15707 | 3'-UTR | T$^S$T$^S$T$^S$T$^S$C$^O$T$^O$T$^O$C$^O$C$^O$A$^O$C$^O$T$^O$G$^O$C$^O$C$^O$C$^S$C$^S$T$^S$C$^S$A$^d$ 2'ME | 78 |
| 15708 | 3'-UTR | T$^S$T$^S$T$^S$T$^S$C$^S$T$^O$T$^O$C$^O$C$^O$A$^O$C$^O$T$^O$G$^O$C$^O$C$^O$C$^S$C$^S$T$^S$C$^S$A$^d$ 2'ME | 78 |
| 13881 | 3'-UTR | T$^O$T$^O$T$^O$T$^O$C$^O$T$^O$T$^O$C$^O$C$^O$A$^O$C$^O$T$^O$G$^S$C$^S$C$^S$C$^S$T$^S$C$^S$A$^d$ 2'ME | 78 |
| 13882 | 3'-UTR | T$^S$T$^S$T$^S$T$^S$C$^S$T$^S$T$^S$C$^S$C$^O$A$^O$C$^O$T$^O$G$^O$C$^O$C$^O$C$^O$C$^O$T$^O$C$^O$A$^d$ 2'ME | 78 |
| 12898 | (scrambled 12633) | & Derivatives: | |
| 12898 | control | T$^S$T$^S$C$^S$T$^S$C$^S$T$^S$T$^S$T$^S$A$^S$G$^S$C$^S$C$^S$T$^S$C$^S$C$^S$C$^S$C$^S$A | 92 |
| 13046 | control | T$^O$T$^O$C$^O$T$^O$C$^O$T$^S$T$^S$T$^S$A$^S$G$^S$C$^S$C$^S$T$^S$C$^O$C$^O$C$^O$C$^O$A$^d$ 2'MO | 92 |
| 13715 | control | T$^O$T$^O$C$^O$T$^O$C$^O$T$^S$T$^S$T$^S$A$^S$G$^S$C$^S$C$^S$T$^S$C$^O$C$^O$C$^O$C$^O$A$^d$ 2'ME | 92 |
| 13912 | control | T$^O$T$^O$C$^O$T$^O$C$^O$T$^O$T$^O$T$^O$A$^O$G$^O$C$^O$C$^S$T$^S$C$^S$C$^S$C$^S$C$^S$A$^d$ 2'ME | 92 |
| 13913 | control | T$^S$T$^S$C$^S$T$^S$C$^S$T$^S$T$^S$T$^O$A$^O$G$^O$C$^O$C$^O$T$^O$C$^O$C$^O$C$^O$C$^O$A$^d$ 2'ME | 92 |
| 15705 | control | T$^S$T$^S$C$^S$T$^S$C$^O$T$^O$T$^O$T$^O$T$^O$A$^O$G$^O$C$^O$C$^O$T$^O$C$^O$C$^S$C$^S$C$^S$A$^d$ 2'ME | 92 |
| 15706 | control | T$^S$T$^S$C$^S$T$^S$C$^O$T$^O$T$^O$T$^O$T$^O$A$^O$G$^O$C$^O$C$^O$T$^O$C$^O$C$^S$C$^S$C$^S$A$^d$ 2'ME | 92 |
| 12628 & | Derivatives: | | |
| 12628 | 5'-UTR | C$^S$C$^S$C$^S$T$^S$C$^S$C$^S$T$^S$G$^S$C$^S$T$^S$C$^S$G$^S$T$^S$C$^S$G$^S$G$^S$T$^S$C$^S$A$^S$C | 73 |
| 13049 | 5'-UTR | C$^O$C$^O$C$^O$T$^O$C$^O$C$^S$T$^S$G$^S$C$^S$T$^S$C$^S$G$^S$T$^S$C$^S$G$^O$G$^O$T$^O$C$^O$A$^O$C$^d$ 2'MO | 73 |
| 13712 | 5'-UTR | C$^O$C$^O$C$^O$T$^O$C$^O$C$^S$T$^S$G$^S$C$^S$T$^S$C$^S$G$^S$T$^S$C$^S$G$^O$G$^O$T$^O$C$^O$A$^O$C$^d$ 2'ME | 73 |
| 13879 | 5'-UTR | C$^O$C$^O$C$^O$T$^O$C$^O$C$^O$T$^O$G$^O$C$^O$T$^O$C$^O$G$^S$T$^S$C$^S$G$^S$G$^S$T$^S$C$^S$A$^S$C$^d$ 2'ME | 73 |
| 13880 | 5'-UTR | C$^S$C$^S$C$^S$T$^S$C$^S$C$^S$T$^S$G$^S$C$^O$T$^O$C$^O$G$^O$T$^O$C$^O$G$^O$G$^O$T$^O$C$^O$A$^O$C$^d$ 2'ME | 73 |
| 12894 | (scrambled 12628) | & Derivatives: | |
| 12894 | | C$^S$C$^S$C$^S$G$^S$G$^S$C$^S$C$^S$T$^S$T$^S$T$^S$T$^S$G$^S$A$^S$C$^S$C$^S$G$^S$C$^S$C$^S$T$^S$C | 87 |
| 13713 | | C$^O$C$^O$C$^O$G$^O$G$^O$C$^S$C$^S$T$^S$T$^S$T$^S$T$^S$G$^S$A$^S$C$^S$C$^O$G$^O$C$^O$C$^O$T$^O$C$^d$ 2'ME | 87 |
| 13048 | | C$^O$C$^O$C$^O$G$^O$G$^O$C$^S$C$^S$T$^S$T$^S$T$^S$T$^S$G$^S$A$^S$C$^S$C$^O$G$^O$C$^O$C$^O$T$^O$C$^d$ 2'MO | 87 |
| 12635 & | Derivatives: | | |
| 12635 | | C$^S$T$^S$T$^S$C$^S$C$^S$C$^S$A$^S$C$^S$T$^S$C$^S$C$^S$A$^S$G$^S$C$^S$A$^S$C$^S$A$^S$T$^S$T$^S$G | 80 |
| 15711 | | C$^S$T$^S$T$^S$C$^S$C$^S$C$^S$A$^S$C$^S$T$^S$C$^S$C$^S$A$^S$G$^S$C$^S$A$^S$C$^S$A$^S$T$^S$T$^S$G 2'ME | 80 |
| 15712 | | C$^S$T$^S$T$^S$C$^S$C$^S$C$^S$A$^S$C$^S$T$^S$C$^S$C$^S$A$^S$G$^S$C$^S$A$^S$C$^S$A$^S$T$^S$T$^S$G$^d$ 2'ME | 80 |
| 15709 | (scrambled 12635) | & Derivatives: | |
| 15709 | | T$^S$T$^S$C$^S$T$^S$C$^S$A$^S$C$^S$C$^S$C$^S$A$^S$C$^S$C$^S$A$^S$C$^S$G$^S$T$^S$A$^S$C$^S$G$^S$T 2'ME | 117 |
| 15710 | | T$^S$T$^S$C$^S$T$^S$C$^O$A$^O$C$^O$C$^O$C$^O$A$^O$C$^O$C$^O$A$^O$C$^O$G$^O$T$^S$A$^S$C$^S$G$^S$T 2'ME | 117 |

*Phosphorothioate linkages are indicated by "$^S$", whereas phosphodiester linkages are signified by "$^O$", emboldened residues comprise the additional indicated modifications:
2'MO = 2'-methoxy-;
2'-ME = 2'-methoxyethoxy-.

TABLE 16

Additional Oligonucleotides Targeted to Rat c-fos

| ISIS # | Target | Oligonucleotide Sequence (5' -> 3'). and Chemical Modifications* | SEQ ID NO: |
|---|---|---|---|
| 11256 | & Derivatives: | | 106 |
| 11256 | 3'-UTR | $C^SA^SG^SG^SC^SC^ST^SG^SG^SC^ST^SC^SA^SC^SA^ST^SG^SC^ST^SA$ | 106 |
| 13051 | 3'-UTR | $C^OA^OG^OG^OC^OC^ST^SG^SG^SC^ST^SC^SA^SC^SA^OT^OG^OC^OT^OA^d$ 2'MO | 106 |
| 13718 | 3'-UTR | $C^SA^SG^SG^SC^SC^ST^SG^SG^SC^ST^SC^SA^SC^SA^ST^SG^SC^ST^SA^d$ 2'ME | 106 |
| 13877 | 3'-UTR | $C^OA^OG^OG^OC^OC^OT^OG^OG^OC^OT^OC^OA^SC^SA^ST^SG^SC^ST^SA^d$ 2'ME | 106 |
| 13878 | 3'-UTR | $C^OA^OG^OG^OC^OC^OT^OG^OG^SC^ST^SC^SA^SC^SA^ST^SG^SC^ST^SA^d$ 2'ME | 106 |
| 12703 | (Scrambled 11256) | & Derivatives: | |
| 12703 | control | $A^SC^SG^ST^SC^SG^SA^SG^SC^SG^SC^SA^SC^SC^SG^ST^SC^SA^ST^ST$ | 114 |
| 13050 | control | $A^OC^OG^CT^OC^OG^SA^SG^SC^SG^SC^SA^SC^SC^SG^OT^OC^OA^OT^OT^d$ 2'MO | 114 |
| 13719 | control | $A^SC^SG^ST^SC^SG^SA^SG^SC^SG^SC^SA^SC^SC^SG^ST^SC^SA^ST^ST^d$ 2'ME | 114 |
| 11254 | & Derivatives: | | |
| 11254 | 3'-UTR | $T^SC^ST^SA^SC^SG^SG^SG^SA^SA^SC^SC^SC^ST^SC^SG^SA^SG^SG$ | 104 |
| 13053 | 3'-UTR | $T^OC^OT^OA^OC^OG^SG^SG^SA^SA^SC^SC^SC^SC^ST^OC^OG^OA^OG^OG^d$ 2'MO | 104 |
| 13716 | 3'-UTR | $T^SC^ST^SA^SC^SG^SG^SG^SA^SA^SC^SC^SC^SC^ST^SC^SG^SA^SG^SG^d$ 2'ME | 104 |
| 13875 | 3'-UTR | $T^OC^OT^OA^OC^OG^OG^OG^OA^OA^OC^OC^OC^ST^SC^SG^SA^SG^SG^d$ 2'ME | 104 |
| 13876 | 3'-UTR | $T^SC^ST^SA^SC^SG^SG^SG^SA^OA^OC^OC^OC^OC^OT^OC^OG^OA^OG^OG^d$ 2'ME | 104 |
| 12700 | (Scrambled 11254) | & Derivatives: | |
| 12700 | control | $C^SC^SG^SC^SC^SG^SG^ST^SG^SA^SC^ST^SA^ST^SA^SG^SA^SC^SC^SG$ | 109 |
| 13052 | control | $C^OC^OG^OC^OC^OG^SG^ST^SG^SA^SC^ST^SA^ST^SA^OG^OA^OC^OC^OG^d$ 2'MO | 109 |
| 13717 | control | $C^SC^SG^SC^SC^SG^SG^ST^SG^SA^SC^ST^SA^ST^SA^SG^SA^SC^SC^SG^d$ 2'ME | 109 |

*Phosphorothioate and phosphodiester linkages are indicated by "S" and "O", respectively, whereas "d" indicates a dideoxy (chain-terminating) residue; emboldened residues comprise the additional indicated modifications: 2'MO, 2'-methoxy; 2'ME, 2'-methoxyethoxy-.

Example 11

Effect of Oligonucleotides Targeted to AP-1 Subunits on PDGF-Induced Proliferation of Rat Aortic Smooth Muscle Cells In order to evaluate the effect of AP-1 modulation on cell cycle progression, the following study was performed. Cultured rat aortic smooth muscle (RASM) cells are stimulated to proliferate upon contact with platelet-derived growth factor (PDGF). Primary RASM cells (passages 6–8) were synchronized by incubation for 48 hours in DMEM containing 0.1% FBS. The cells were treated for 4 hours with 200 nM ISIS 12633 (SEQ ID NO:78), a 20-mer phosphorothioate oligonucleotide complementary to a portion of the 3' UTR of rat c-jun mRNA, or ISIS 12898 (SEQ ID NO:92), a scrambled control of ISIS 12633. Cells were then contacted with PDGF (10 ng/ml) (R&D Systems, Minneapolis, Minn.), and cell cycle progression was assessed by FACS analysis 24 hours later. At 2 and 6 hours after exposure to PDGF, c-jun mRNA levels were markedly less in ISIS 12633-treated cells as compared to untreated cells or cells treated with ISIS 12898. The decrease in c-jun mRNA levels was associated with a significant decrease in the proportion of cells in the G2/M interface at 24 hours. This result provides evidence of the role of AP-1-mediated gene expression in cellular proliferation and indicate that cell cycle progression can be modulated by preventing expression of one or both of the genes which encode a subunit of AP-1.

Example 12

Effect of Oligonucleotides Targeted to AP-1 Subunits on Enzymes Involved in Metastasis Patients having benign tumors, and primary malignant tumors that have been detected early in the course of their development, may often be successfully treated by the surgical removal of the benign or primary tumor. If unchecked, however, cells from malignant tumors are spread throughout a patient's body through the processes of invasion and metastasis. Invasion refers to the ability of cancer cells to detach from a primary site of attachment and penetrate, e.g., an underlying basement membrane. Metastasis indicates a sequence of events wherein (1) a cancer cell detaches from its extracellular matrices, (2) the detached cancer cell migrates to another portion of the patient's body, often via the circulatory system, and (3) attaches to a distal and inappropriate extracellular matrix, thereby created a focus from which a secondary tumor can arise. Normal cells do not possess the ability to invade or metastasize and/or undergo apoptosis (programmed cell death) if such events occur (Ruoslahti, *Sci. Amer.,* 1996, 275, 72).

The matrix metalloproteinases (MMPs) are a family of enzymes which have the ability to degrade components of the extracellular matrix (Birkedal-Hansen, *Current Op. Biol.,* 1995, 7, 728). Many members of the MMP family have been found to have elevated levels of activity in human tumors as well as other disease states (Stetler-Stevenson et al., *Annu. Rev. Cell Biol.,* 1993, 9, 541; Bernhard et al., *Proc. Natl. Acad. Sci.* (U.S.A.), 1994, 91, 4293). In particular, one member of this family, matrix metalloproteinase-9 (MMP-9), is often found to be expressed only in tumors and other diseased tissues (Himelstein et al., *Invasion & Metastasis,* 1994, 14, 246). Several studies have shown that regulation of the MMP-9 gene may be controlled by the AP-1 transcription factor (Kerr et al., *Science,* 1988, 242, 1242; Kerr et al., *Cell,* 1990, 61, 267; Gum et al., *J. Biol. Chem.,* 1996, 271, 10672; Hua et al., *Cancer Res.,* 1996, 56, 5279). In order to determine whether MMP-9 expression can be influenced by AP-1 modulation, the following experiments were conducted on normal human epidermal keratinocytes (NHEKs). Although NHEKs normally express no detectable MMP-9, MMP-9 can be induced by a number of stimuli, including TPA. ISIS 10582, an oligonucleotide targeted to c-jun, was evaluated for its ability to modulate MMP-9 expression according to the protocols described in Examples 2–3 with the following exceptions: (1) NHEK cells were used instead of A549 cells, (2) the probe used, a PCR product prepared using the published sequence of the MMP-9 gene (Huhtala et al., *J. Biol. Chem.*, 1991, 266:16485; Sato et al., *Oncogene*, 1993, 8:395), is specific for MMP-9 rather than c-jun, and (3) the cells were harvested 24 hours after TPA treatment for 4 hours. The results (Table 17) demonstrate that ISIS 10582 is able to completely inhibit the expression of MMP-9 after induction with TPA.

TABLE 17

Effect of c-jun Oligonucleotide on MMP-9 Expression

| Treatment | MMP-9 |
| --- | --- |
| Basal | 4 |
| TPA - no oligo | 100 |
| 10582: c-jun active | 6 |
| 11562: sense control | 99 |
| 11563: scrambled control | 95 |
| 11564: mismatch control | 89 |

These results demonstrate that c-Jun is required for TPA-mediated induction of MMP-9, and indicate that oligonucleotides targeted to AP-1 subunits can inhibit the expression of MMP family members, thereby modulating the ability of cancer cells to invade other tissues and/or metastasize to other sites in a patient's body.

Example 13

Antagonism of Inducers Other than TPA by Oligonucleotides Targeted to AP-1 Subunits Inducing agents other than TPA function to raise AP-1 levels in vivo. In order to assess the ability of oligonucleotides targeted to AP-1 to antagonize the action of three such inducers, A549 cells were treated and evaluated as in Examples 2 et seq. with the exception that TNF-(δ, IL-1β or TNF-α or IL-1β (each at 10 ng/ml and all from R&D Systems, Minneapolis, Minn.) were used in place of TPA as inducers. The results (Table 18) demonstrate that ISIS 10582 (SEQ ID NO:8, targeted to human c-jun) effectively reduces stimulation of c-Jun by TNF-α, IL-1β or TGF-β. In contrast, a scrambled control oligonucleotide, ISIS 11563 (SEQ ID NO:30), did not reverse the induction of c-Jun.

TABLE 18

Effect of Oligonucleotides Targeted to c-Jun on Induction by TNF-α, IL-1β or TGF-β

| Inducer | Basal | No Oligo | ISIS 10582 | ISIS 11563 |
| --- | --- | --- | --- | --- |
| TNF-α | 5 | 100 | 20 | 98 |
| IL-1β | 9 | 100 | 15 | 94 |
| TGF-β | 2 | 100 | 95 | 99 |

What is claimed is:

1. An antisense oligonucleotide consisting of a nucleic acid sequence selected from a group consisting of SEQ ID NO: 10, 11, 12, 14, 15, 16, 17, 18, 19, 20, 21, 22, 23, 24, 25, 27, 120, 121, 122, 123, 131, 132, 133, 134, 135, 136, 137 and 138 wherein said oligonucleotide inhibits the expression of c-Fos protein.

2. The antisense oligonucleotide of claim 1 wherein said antisense oligonucleotide comprises at least one 2' methoxyethoxy residue.

3. The antisense oligonucleotide of claim 1 wherein said antisense oligonucleotide comprises two or more chemically distinct regions.

4. The antisense oligonucleotide of claim 3 wherein said antisense oligonucleotide is a hemimer or a gapmer.

5. The antisense oligonucleotide of claim 3 wherein one of said chemically distinct regions comprises one or more 2'-methoxyethoxy residues.

6. The antisense oligonucleotide of claim 1 wherein said antisense oligonucleotide comprises a peptide nucleic acid.

7. The antisense oligonucleotide of claim 1, wherein at least one covalent linkage of said nucleic acid sequence is a modified covalent linkage.

8. The antisense oligonucleotide of claim 7, wherein said modified covalent linkage is selected from the group consisting of a phosphorothioate linkage, a phosphotriester linkage, a methyl phosphonate linkage, a methylene (methylimino) linkage, a morpholino linkage, an amide linkage, a polyamide linkage, a short chain alkyl intersugar linkage, a cycloalkyl intersugar linkage, a short chain heteroatomic intersugar linkage and a heterocyclic intersugar linkage.

9. The antisense oligonucleotide of claim 1, wherein at least one nucleotide of said nucleic acid sequence has a modified sugar moiety.

10. The antisense oligonucleotide of claim 9, wherein said modified sugar moiety is a modification at the 2' position of any nucleotide, the 3' position of the 3' terminal nucleotide or the 5' position of the 5' terminal oligonucleotide.

11. The antisense oligonucleotide of claim 10, wherein said modification is selected from the group consisting of a substitution of an azido group for a 3' hydroxyl group and a substitution of a hydrogen atom for a 3' or 5' hydroxyl group.

12. The antisense oligonucleotide of claim 10, wherein said modification is a substitution or addition at the 2' position of a moiety selected from the group consisting of —OH, —SH, —SCH$_3$, —F, —OCN, —OCH$_3$OCH$_3$, —OCH$_3$O(CH$_2$)$_n$CH$_3$, —O(CH$_2$)$_n$NH$_2$ or —O(CH$_2$)$_n$CH$_3$ where n is from 1 to about 10, a C$_1$ to C$_{10}$ lower alkyl group, an alkoxyalkoxy group, a substituted lower alkyl group, a substituted alkaryl group, a substituted aralkyl group, —Cl, —Br, —CN, —CF$_3$, —OCF$_3$, an —O-alkyl group, an —S-alkyl group, an N-alkyl group, an O-alkenyl group, an S-alkenyl group, an N-alkenyl group, —SOCH$_3$, —SO$_2$CH$_3$, —ONO$_2$, —NO$_2$, —N$_3$, —NH$_2$, a heterocycloalkyl group, a heterocycloalkaryl group, an aminoalkylamino group, a polyalkylamino group, a substituted silyl group, an RNA cleaving group, a reporter group, a DNA intercalating group, a group for improving the pharmacokinetic properties of an oligonucleotide, a group for improving the pharmacodynamic properties of an oligonucleotide, a methoxyethoxy group and a methoxy group.

13. The antisense oligonucleotide of claim 1, wherein at least one nucleotide of said nucleic acid sequence has a modified nucleobase.

14. The antisense oligonucleotide of claim 13, wherein said modified nucleobase is selected from the group consisting of hypoxanthine, 5-methylcytosine, 5-hydroxymethylcytosine, glycosyl 5-hydroxymethylcytosine, gentiobiosyl 5-hydroxymethylcytosine, 5-bromouracil, 5-hydroxymethyluracil, 6-methyladenine, N$^6$-(6-aminohexyl)adenine, 8-azaguanine, 7-deazaguanine and 2,6-diaminopurine.

15. A pharmaceutical composition comprising the oligonucleotide of claim 1 and a pharmaceutically acceptable carrier.

16. The pharmaceutical composition of claim 15 further comprising a chemotherapeutic agent.

17. A pharmaceutical composition comprising
(a) an oligonucleotide of claim 1;
(b) an oligonucleotide selected from the group consisting of SEQ ID Nos: 1, 3, 4, 5, 6, 7, 8, 9, 36 and 37; and
(c) a pharmaceutically acceptable carrier.

18. A pharmaceutical composition comprising
(a) a chemotherapeutic agent;
(b) an oligonucleotide of claim 1;
(c) an oligonucleotide selected from the group consisting of SEQ ID Nos: 1, 3, 4, 5, 6, 7, 8, 9, 36 and 37; and
(d) a pharmaceutically acceptable carrier.

19. A pharmaceutical composition comprising the oligonucleotide of claim 2 and a pharmaceutically acceptable carrier.

20. A pharmaceutical composition comprising
(a) a chemotherapeutic agent;
(b) the oligonucleotide of claim 2; and
(c) a pharmaceutically acceptable carrier.

21. An antisense oligonucleotide consisting of a nucleic acid sequence selected from a group consisting of SEQ ID NO: 1, 3, 4, 5, 6, 7, 8, 9, 36 and 37, wherein said oligonucleotide inhibits the expression of c-Jun protein.

22. The antisense oligonucleotide of claim 21 wherein said antisense oligonucleotide comprises at least one 2'-methoxyethoxy residue.

23. The antisense oligonucleotide of claim 21 wherein said antisense oligonucleotide comprises two or more chemically distinct regions.

24. The antisense oligonucleotide of claim 23, wherein said antisense oligonucleotide is a hemimer or a gapmer.

25. The antisense oligonucleotide of claim 23, wherein one of said chemically distinct regions comprises one or more 2'-methoxyethoxy residues.

26. The antisense oligonucleotide of claim 21 wherein said antisense oligonucleotide comprises a peptide nucleic acid.

27. The antisense oligonucleotide of claim 21, wherein at least one covalent linkage of said nucleic acid sequence is a modified covalent linkage.

28. The antisense oligonucleotide of claim 27, wherein said modified covalent linkage is selected from the group consisting of a phosphorothioate linkage, a phosphotriester linkage, a methyl phosphonate linkage, a methylene (methylimino) linkage, a morpholino linkage, an amide linkage, a polyamide linkage, a short chain alkyl intersugar linkage, a cycloalkyl intersugar linkage, a short chain heteroatomic intersugar linkage and a heterocyclic intersugar linkage.

29. The antisense oligonucleotide of claim 21, wherein at least one nucleotide of said nucleic acid sequence has a modified sugar moiety.

30. The antisense oligonucleotide of claim 29, wherein said modified sugar moiety is a modification at the 2' position of any nucleotide, the 3' position of the 3' terminal nucleotide or the 5'position of the 5' terminal oligonucleotide.

31. The antisense oligonucleotide of claim 30, wherein said modification is selected from the group consisting of a substitution of an azido group for a 3' hydroxyl group and a substitution of a hydrogen atom for a 3' or 5' hydroxyl group.

32. The antisense oligonucleotide of claim 30, wherein said modification is a substitution or addition at the 2' position of a moiety selected from the group consisting of —OH, —SH, —SCH$_3$, —F, —OCN, —OCH$_3$OCH$_3$, —OCH$_3$O(CH$_2$)$_n$CH$_3$, —O(CH$_2$)$_n$NH$_2$ or —O(CH$_2$)$_n$CH$_3$ where n is from 1 to about 10, a C$_1$ to C$_{10}$ lower alkyl group, an alkoxyalkoxy group, a substituted lower alkyl group, a substituted alkaryl group, a substituted aralkyl group, —Cl, —Br, —CN, —CF$_3$, —OCF$_3$, an —O-alkyl group, an —S-alkyl group, an N-alkyl group, an O-alkenyl group, an S-alkenyl group, an N-alkenyl group, —SOCH$_3$, —SO$_2$CH$_3$, —ONO$_2$, —NO$_2$, —N$_3$, —NH$_2$, a heterocycloalkyl group, a heterocycloalkaryl group, an aminoalkylamino group, a polyalkylamino group, a substituted silyl group, an RNA cleaving group, a reporter group, a DNA intercalating group, a group for improving the pharmacokinetic properties of an oligonucleotide, a group for improving the pharmacodynamic properties of an oligonucleotide, a methoxyethoxy group and a methoxy group.

33. The antisense oligonucleotide of claim 21, wherein at least one nucleotide of said nucleic acid sequence has a modified nucleobase.

34. The antisense oligonucleotide of claim 33, wherein said modified nucleobase is selected from the group consisting of hypoxanthine, 5-methylcytosine, 5-hydroxymethylcytosine, glycosyl 5-hydroxymethylcytosine, gentiobiosyl 5-hydroxymethylcytosine, 5-bromouracil, 5-hydroxymethyluracil, 6-methyladenine, N$^6$-(6-aminohexyl)adenine, 8-azaguanine, 7-deazaguanine and 2,6-diaminopurine.

35. A pharmaceutical composition comprising the oligonucleotide of claim 21 and a pharmaceutically acceptable carrier.

36. The pharmaceutical composition of claim 21 further comprising a chemotherapeutic agent.

37. A pharmaceutical composition comprising the oligonucleotide of claim 22 and a pharmaceutically acceptable carrier.

38. A pharmaceutical composition comprising
(a) a chemotherapeutic agent;
(b) the oligonucleotide of claim 22; and
(c) a pharmaceutically acceptable carrier.

39. An antisense oligonucleotide consisting of a nucleobase sequence that is 8 to 30 nucleotides in length is specifically hybridizable with at least a portion of the sequence

3'- ACGGGGAGTCGGGGCTGCCAGAGAGAAGT-5' (SEQ ID NO: 139).

40. The antisense oligonucleotide of claim 39 comprising the sequence

```
5'- TGCCCCTCAGCCCCCGACGC       -3'  SEQ ID NO: 9,
5'-       TCAGCCCCCGACGGTCTCTC -3'  SEQ ID NO: 8,
or
5'-             CCCCCGACGGTCTCTCTTCA-3'  SEQ ID NO: 7.
```

41. A method of inhibiting the expression of a c-Fos protein in cells or tissues comprising contacting said cells or tissues with an oligonucleotide of claim 1 so that the expression of said c-Fos protein is inhibited.

42. A method of inhibiting the expression of a c-Fos protein in cells or tissues comprising contacting said cells or tissues with an oligonucleotide of claim 2 so that the expression of said c-Fos protein is inhibited.

43. A method of inhibiting the expression of a c-Jun protein in cells or tissues comprising contacting said cells or tissues with an oligonucleotide of claim 21 so that the expression of said c-Jun protein is inhibited.

44. A method of inhibiting the expression of a c-Jun protein in cells or tissues comprising contacting said cells or tissues with an oligonucleotide of claim 22 so that the expression of said c-Jun protein is inhibited.

* * * * *

SEQUENCE LISTING (1) GENERAL INFORMATION:

(iii) NUMBER OF SEQUENCES: 139

(2) INFORMATION FOR SEQ ID NO:1:

(i) SEQUENCE CHARACTERISTICS:
      (A) LENGTH: 20
      (B) TYPE: Nucleic Acid
      (C) STRANDEDNESS: Single
      (D) TOPOLOGY: Linear (iv) ANTI-SENSE: Yes (xi) SEQUENCE DESCRIPTION: SEQ ID NO: 1:

GCCACACTCA GTGCAACTCT                        20

(2) INFORMATION FOR SEQ ID NO: 2:

(i) SEQUENCE CHARACTERISTICS:
      (A) LENGTH: 20
      (B) TYPE: Nucleic Acid
      (C) STRANDEDNESS: Single
      (D) TOPOLOGY: Linear (iv) ANTI-SENSE: Yes (xi) SEQUENCE DESCRIPTION: SEQ ID NO: 2:

CGCACCTCCA CTCCCGCCTC                        20

(2) INFORMATION FOR SEQ ID NO: 3:

(i) SEQUENCE CHARACTERISTICS:
      (A) LENGTH: 20

(B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 3:

ACCAGCCCGG GAGCCACAGG                                                           20

(2) INFORMATION FOR SEQ ID NO: 4:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 4:

GCTGCGCCGC CGACGTGACG                                                           20

(2) INFORMATION FOR SEQ ID NO: 5:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 5:

CGCCCCGCCG CCGCTGCTCA                                                           20

(2) INFORMATION FOR SEQ ID NO: 6:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 6:

GTGTCTCGCC GGGCATCTCG                                                           20

(2) INFORMATION FOR SEQ ID NO: 7:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 7:

CCCCCGACGG TCTCTCTTCA                                                           20

(2) INFORMATION FOR SEQ ID NO: 8:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 8:

TCAGCCCCCG ACGGTCTCTC                    20

(2) INFORMATION FOR SEQ ID NO: 9:

(i) SEQUENCE CHARACTERISTICS:
       (A) LENGTH: 20
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 9:

TGCCCCTCAG CCCCCGACGG                    20

(2) INFORMATION FOR SEQ ID NO: 10:

(i) SEQUENCE CHARACTERISTICS:
       (A) LENGTH: 20
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 10:

TGCTCGCTGC AGATGCGGTT                    20

(2) INFORMATION FOR SEQ ID NO: 11:

(i) SEQUENCE CHARACTERISTICS:
       (A) LENGTH: 20
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 11:

CGGTCACTGC TCGTTCGCTG                    20

(2) INFORMATION FOR SEQ ID NO: 12:

(i) SEQUENCE CHARACTERISTICS:
       (A) LENGTH: 20
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 12:

CATCGTGGCG GTTAGGCAAA                    20

(2) INFORMATION FOR SEQ ID NO: 13:

(i) SEQUENCE CHARACTERISTICS:
       (A) LENGTH: 20
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 13:

GAGAACATCA TCGTGGCGGT                    20

(2) INFORMATION FOR SEQ ID NO: 14:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 14:

ACCGTGGGAA TGAAGTTGGC                                               20

(2) INFORMATION FOR SEQ ID NO: 15:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 15:

AGCTCCCTCC TCCGGTTGCG                                               20

(2) INFORMATION FOR SEQ ID NO: 16:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 16:

TTGCAGGCAG GTCGGTGAGC                                               20

(2) INFORMATION FOR SEQ ID NO: 17:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 17:

TGGCACGGAG CGGGCTGTCT                                               20

(2) INFORMATION FOR SEQ ID NO: 18:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 18:

TGCTGCTGCC CTTGCGGTGG                                               20

(2) INFORMATION FOR SEQ ID NO: 19:

(i) SEQUENCE CHARACTERISTICS:
        (A) LENGTH: 20

```
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 19:

CCTCACAGGG CCAGCAGCGT                                                        20

(2) INFORMATION FOR SEQ ID NO: 20:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 20:

GGTGCCGGCT GCCTCCCCTT                                                        20

(2) INFORMATION FOR SEQ ID NO: 21:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 21:

AAGTCCTTGA GGCCCACAGC                                                        20

(2) INFORMATION FOR SEQ ID NO: 22:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 22:

CCCCTCCAGC AGCTACCCTT                                                        20

(2) INFORMATION FOR SEQ ID NO: 23:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 23:

TCCCGTCCCC AGAAGCAGTA                                                        20

(2) INFORMATION FOR SEQ ID NO: 24:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes
```

(xi) SEQUENCE DESCRIPTION: SEQ ID NO: 24:

CGCGCCCGGC CTGAAAATTT                    20

(2) INFORMATION FOR SEQ ID NO: 25:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 25:

CCTGCCTCGG CCTCCCAAAG                    20

(2) INFORMATION FOR SEQ ID NO: 26:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 26:

CCCCCACTTC CGCCCACTAT                    20

(2) INFORMATION FOR SEQ ID NO: 27:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 27:

TGGTGCCTGC GTGATACTCG                    20

(2) INFORMATION FOR SEQ ID NO: 28:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 28:

CCCTCCCAGG CTCAAGTCAT                    20

(2) INFORMATION FOR SEQ ID NO: 29:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 29:

GAGAGACCGT CGGGGGCTGA                    20

(2) INFORMATION FOR SEQ ID NO:30:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 30:

CACCTCCACG CGCTTCTGGC                                      20

(2) INFORMATION FOR SEQ ID NO: 31:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 31:

TCGGCACCTG AAGGACTTTC                                      20

(2) INFORMATION FOR SEQ ID NO: 32:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 32:

GCTGTGGGCC TCAAGGACTT                                      20

(2) INFORMATION FOR SEQ ID NO: 33:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 33:

ATGTGCTAGA TGCGCAAAGT                                      20

(2) INFORMATION FOR SEQ ID NO: 34:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 34:

ACGTCCGATT CCGAGCGCAA                                      20

(2) INFORMATION FOR SEQ ID NO: 35:

(i) SEQUENCE CHARACTERISTICS:
        (A) LENGTH: 20

(B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 35:

CAGTGGCCAT CAAACCCGTG                                                    20

(2) INFORMATION FOR SEQ ID NO: 36:

(i) SEQUENCE CHARACTERISTICS:
            (A) LENGTH: 16
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 36:

CACTCAGTGC AACTCT                                                        16

(2) INFORMATION FOR SEQ ID NO: 37:

(i) SEQUENCE CHARACTERISTICS:
            (A) LENGTH: 16
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 37:

CCTCCACTCC CGCCTC                                                        16

(2) INFORMATION FOR SEQ ID NO: 38:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 38:

CTCGCCCAAC TTCAGCCGCC                                                    20

(2) INFORMATION FOR SEQ ID NO: 39:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 39:

CCAGTCCCAG CAACAGCGGC                                                    20

(2) INFORMATION FOR SEQ ID NO: 40:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes -continued (xi) SEQUENCE DESCRIPTION: SEQ ID NO: 40:

GCAACAGCGC GCCGGGAAGC                                                    20

(2) INFORMATION FOR SEQ ID NO: 41:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 41:

CCGGCGACGC CAGCTTGAGC                                                    20

(2) INFORMATION FOR SEQ ID NO: 42:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 42:

GGCTGTGCCG CGGAGGTGAC                                                    20

(2) INFORMATION FOR SEQ ID NO: 43:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 43:

CGCCCCACCG CCGCTGCTCA                                                    20

(2) INFORMATION FOR SEQ ID NO: 44:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 44:

AGCCCGGCCG CGCCATAGGA                                                    20

(2) INFORMATION FOR SEQ ID NO: 45:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 45:

CTGCACCGGG ATCTGTTGGG                                                    20

(2) INFORMATION FOR SEQ ID NO: 46:

(i) SEQUENCE CHARACTERISTICS:
        (A) LENGTH: 23
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 46:

GGCGGCGTCT CTCCCGGCAT CTC                             23

(2) INFORMATION FOR SEQ ID NO: 47:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 47:

TGGAGGCGGC AATGCGGTTC                                   20

(2) INFORMATION FOR SEQ ID NO: 48:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 48:

CCCTGAGCAT GTTGGCCGTG                                   20

(2) INFORMATION FOR SEQ ID NO: 49:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 49:

CAAAGCCAGG CGCGCCACGT                                   20

(2) INFORMATION FOR SEQ ID NO: 50:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 50:

TTGAGAGAGG CAGGCCAGGG                                   20

(2) INFORMATION FOR SEQ ID NO: 51:

(i) SEQUENCE CHARACTERISTICS:
        (A) LENGTH: 20

(B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 51:

TGGACTTGTG TGTTGCCGGG                                               20

(2) INFORMATION FOR SEQ ID NO: 52:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 52:

TCCATGGGTC CCTGCTTTGA                                               20

(2) INFORMATION FOR SEQ ID NO: 53:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 53:

TGGTCGCGCG CGGGCACAGC                                               20

(2) INFORMATION FOR SEQ ID NO: 54:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 54:

AGCTCCCTCC TCCGATTCCG                                               20

(2) INFORMATION FOR SEQ ID NO: 55:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 55:

GCTCTGTGAC CATGGGCCCC                                               20

(2) INFORMATION FOR SEQ ID NO: 56:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 56:

GAACCGCCGG CTCTATCCAG                                       20

(2) INFORMATION FOR SEQ ID NO: 57:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 57:

GCCCCTGCGA GTCACACCCC                                       20

(2) INFORMATION FOR SEQ ID NO: 58:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 58:

TAAGGCTGCT CTGACCGCGC                                       20

(2) INFORMATION FOR SEQ ID NO: 59:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 59:

CGCCCGCAGC ACCCTCCTCC                                       20

(2) INFORMATION FOR SEQ ID NO: 60:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 60:

CAGGCGCTGC TCCGGAGTCT                                       20

(2) INFORMATION FOR SEQ ID NO: 61:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 61:

TCCCTTGAAT TCCGCAGCGC                                       20

(2) INFORMATION FOR SEQ ID NO: 62:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 62:

AGCGGAGGTG AGCGAGGAGG                                      20

(2) INFORMATION FOR SEQ ID NO: 63:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 63:

CCCCAGCCCA CAAAGGTCCA                                      20

(2) INFORMATION FOR SEQ ID NO: 64:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 64:

TGCTCAAGGA CCCTGCGCCC                                      20

(2) INFORMATION FOR SEQ ID NO: 65:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 65:

GGGAAGCCAA GGTCATCGGG                                      20

(2) INFORMATION FOR SEQ ID NO: 66:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 66:

TGCTGCTGCC CTTTCGGTGG                                      20

(2) INFORMATION FOR SEQ ID NO: 67:

(i) SEQUENCE CHARACTERISTICS:
        (A) LENGTH: 20

(B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 67:

CTGGATGCCG GCTGCCTTGC                                               20

(2) INFORMATION FOR SEQ ID NO: 68:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 68:

CAGCTCGGGA AGTGGCACGT                                               20

(2) INFORMATION FOR SEQ ID NO: 69:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 69:

GGAACACGCT ATTGCCAGGA                                               20

(2) INFORMATION FOR SEQ ID NO: 70:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 70:

CGGCGGCGCA GACCAGTCGT                                               20

(2) INFORMATION FOR SEQ ID NO: 71:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 71:

GGCATCGTCG TAGAAGGTCG                                               20

(2) INFORMATION FOR SEQ ID NO: 72:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 72:

GGAGGTGCGG CTTCAGATTG                                           20

(2) INFORMATION FOR SEQ ID NO: 73:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 73:

CCCTCCTGCT CGTCGGTCAC                                           20

(2) INFORMATION FOR SEQ ID NO: 74:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 74:

ACTGACTGGT TGTGCCGCGG                                           20

(2) INFORMATION FOR SEQ ID NO: 75:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 75:

CGCTGTAGCC GCCGCCGCCG                                           20

(2) INFORMATION FOR SEQ ID NO: 76:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 76:

CCTTGATCCG CTCCTGAGAC                                           20

(2) INFORMATION FOR SEQ ID NO: 77:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 77:

GCCAGCTCGG AGTTTTGCGC                                           20

(2) INFORMATION FOR SEQ ID NO: 78:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 78:

TTTTCTTCCA CTGCCCCTCA                                      20

(2) INFORMATION FOR SEQ ID NO: 79:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 79:

CCCTTGGCTT CAGTACTCGG                                      20

(2) INFORMATION FOR SEQ ID NO: 80:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 80:

CTTCCCACTC CAGCACATTG                                      20

(2) INFORMATION FOR SEQ ID NO: 81:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 81:

GCACAGCCCG TTCGCAAAGC                                      20

(2) INFORMATION FOR SEQ ID NO: 82:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 82:

AATGCAGCAG AGAGGTTGGG                                      20

(2) INFORMATION FOR SEQ ID NO: 83:

(i) SEQUENCE CHARACTERISTICS:
        (A) LENGTH: 20

(B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 83:

GACGGGAGGG ACTACAGGCT                              20

(2) INFORMATION FOR SEQ ID NO: 84:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 84:

TCTGGACTTG TGGGTTGCTG                              20

(2) INFORMATION FOR SEQ ID NO: 85:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 85:

TAAACGATCA CAGCGCATGC                              20

(2) INFORMATION FOR SEQ ID NO: 86:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 86:

GGGAGGACGA GCAGCCAGTG                              20

(2) INFORMATION FOR SEQ ID NO: 87:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 87:

CCCGGCCTTT TGACCGCCTC                              20

(2) INFORMATION FOR SEQ ID NO: 88:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 88:

CCGCCTCCCC GGCCTTTTGA                                       20

(2) INFORMATION FOR SEQ ID NO: 89:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 89:

CCGTCGTGGT CCTCCGTGAC                                       20

(2) INFORMATION FOR SEQ ID NO: 90:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 90:

GTGACCGACG AGCAGGAGGG                                       20

(2) INFORMATION FOR SEQ ID NO: 91:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 91:

AAAAGAAGGT GACGGGGAGT                                       20

(2) INFORMATION FOR SEQ ID NO: 92:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 92:

TTCTCTTTTA GCCTCCCCCA                                       20

(2) INFORMATION FOR SEQ ID NO: 93:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 93:

TCCCCCATTC TCTTTTAGCC                                       20

(2) INFORMATION FOR SEQ ID NO: 94:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 94:

TTATCATCGA CAGCGCCACA                                        20

(2) INFORMATION FOR SEQ ID NO: 95:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 95:

TGAGGGGCAG TGGAAGAAAA                                        20

(2) INFORMATION FOR SEQ ID NO: 96:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 96:

GTTCTCGGCT CCGCCGGCTC                                        20

(2) INFORMATION FOR SEQ ID NO: 97:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 97:

CATCATGGTC GTGGTTTGGG                                        20

(2) INFORMATION FOR SEQ ID NO: 98:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 98:

TCCGCGTTGA AACCCGAGAA                                        20

(2) INFORMATION FOR SEQ ID NO: 99:

(i) SEQUENCE CHARACTERISTICS:
        (A) LENGTH: 20

(B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 99:

TGGGCTGGTG GAGATGGCTG                                               20

(2) INFORMATION FOR SEQ ID NO: 100:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 100:

CGATGCTCTG CGCTCTGCCG                                               20

(2) INFORMATION FOR SEQ ID NO: 101:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 101:

TTCGGTGGGC AGCTGCGCAG                                               20

(2) INFORMATION FOR SEQ ID NO: 102:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 102:

CAGGGCTAGC AGTGTGGGCG                                               20

(2) INFORMATION FOR SEQ ID NO: 103:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 103:

CCAGCTCAGT CAGTGCCGGC                                               20

(2) INFORMATION FOR SEQ ID NO: 104:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 104:

TCTACGGGAA CCCCTCGAGG                    20

(2) INFORMATION FOR SEQ ID NO: 105:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 105:

CTCCATGCGG TTGCTTTTGA                    20

(2) INFORMATION FOR SEQ ID NO: 106:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 106:

CAGGCCTGGC TCACATGCTA                    20

(2) INFORMATION FOR SEQ ID NO: 107:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 107:

AGATGCCCTT GGGGAGCTCC                    20

(2) INFORMATION FOR SEQ ID NO: 108:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 108:

TGACTATAGA CCGCCGCCGG                    20

(2) INFORMATION FOR SEQ ID NO: 109:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 109:

CCGCCGGTGA CTATAGACCG                    20

(2) INFORMATION FOR SEQ ID NO: 110:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 110:

TCAACCGGTA CGCCACGTGG                         20

(2) INFORMATION FOR SEQ ID NO: 111:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 111:

CCTCGAGGGG TTCCCGTAGA                         20

(2) INFORMATION FOR SEQ ID NO: 112:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 112:

GTCCGGACCG AGTGTACGAT                         20

(2) INFORMATION FOR SEQ ID NO: 113:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 113:

GCGCACCGTC ATTACGTCGA                         20

(2) INFORMATION FOR SEQ ID NO: 114:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 114:

ACGTCGAGCG CACCGTCATT                         20

(2) INFORMATION FOR SEQ ID NO: 115:

(i) SEQUENCE CHARACTERISTICS:
        (A) LENGTH: 20

-continued (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 115:

CACGCGTGCC TGACTTGGTA                                              20

(2) INFORMATION FOR SEQ ID NO: 116:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 116:

TAGCATGTGA GCCAGGCCTG                                              20

(2) INFORMATION FOR SEQ ID NO: 117:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 117:

TTCTCACCCA CCACGTACGT                                              20

(2) INFORMATION FOR SEQ ID NO: 118:

(i) SEQUENCE CHARACTERISTICS:
            (A) LENGTH: 16
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 118:

TGCGGGTGAG TGGTAG                                                  16

(2) INFORMATION FOR SEQ ID NO: 119:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 119:

GCCGCGGGAC CAGCCCCAGC                                              20

(2) INFORMATION FOR SEQ ID NO: 120:

(i) SEQUENCE CHARACTERISTICS:
            (A) LENGTH: 16
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 120:

TGCGGGTGAG TGGTAG                                                16

(2) INFORMATION FOR SEQ ID NO: 121:

(i) SEQUENCE CHARACTERISTICS:
        (A) LENGTH: 16
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 121:

CGCTGCAGAT GCGGTT                                                16

(2) INFORMATION FOR SEQ ID NO: 122:

(i) SEQUENCE CHARACTERISTICS:
        (A) LENGTH: 16
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 122:

CCGCCGGCTC AGTCTT                                                16

(2) INFORMATION FOR SEQ ID NO: 123:

(i) SEQUENCE CHARACTERISTICS:
        (A) LENGTH: 16
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 123:

CATCGTGGCG GTTAGG                                                16

(2) INFORMATION FOR SEQ ID NO: 124:

(i) SEQUENCE CHARACTERISTICS:
        (A) LENGTH: 30
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 124:

CCATCTTAAT AAATAAATTA AAAACACAAT                                 30

(2) INFORMATION FOR SEQ ID NO: 125:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 125:

AAATAAATTA AAAACACAAT                                            20

(2) INFORMATION FOR SEQ ID NO: 126:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 126:

AATTAAAAAC ACAATAAAAC                                          20

(2) INFORMATION FOR SEQ ID NO: 127:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 127:

ATATAAATAT CTGAGAATCC                                          20

(2) INFORMATION FOR SEQ ID NO: 128:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 128:

ATCTGAGAAT CCATCTTAAT                                          20

(2) INFORMATION FOR SEQ ID NO: 129:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 129:

AAATATAAAT ATCTGAGAAT                                          20

(2) INFORMATION FOR SEQ ID NO: 130:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 130:

AAGACCTCAA GGTAGAAAAA                                          20

(2) INFORMATION FOR SEQ ID NO: 131:

(i) SEQUENCE CHARACTERISTICS:
        (A) LENGTH: 30

```
         (B) TYPE: Nucleic Acid
         (C) STRANDEDNESS: Single
         (D) TOPOLOGY: Linear (iv) ANTI-SENSE: Yes (xi) SEQUENCE DESCRIPTION:  SEQ ID NO: 131:

CCATCTTAAT AAATAAATTA AAAACACAAT                                    30

(2) INFORMATION FOR SEQ ID NO: 132:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION:  SEQ ID NO: 132:

AAATAAATTA AAAACACAAT                                               20

(2) INFORMATION FOR SEQ ID NO: 133:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION:  SEQ ID NO: 133:

AATTAAAAAC ACAATAAAAC                                               20

(2) INFORMATION FOR SEQ ID NO: 134:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION:  SEQ ID NO: 134:

ATATAAATAT CTGAGAATCC                                               20

(2) INFORMATION FOR SEQ ID NO: 135:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION:  SEQ ID NO: 135:

ATATAAATAT CTGAGAATCC                                               20

(2) INFORMATION FOR SEQ ID NO: 136:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes
```

```
      (xi) SEQUENCE DESCRIPTION:  SEQ ID NO: 136:

ATCTGAGAAT CCATCTTAAT                                                  20

(2) INFORMATION FOR SEQ ID NO: 137:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION:  SEQ ID NO: 137:

AAATATAAAT ATCTGAGAAT                                                  20

(2) INFORMATION FOR SEQ ID NO: 138:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION:  SEQ ID NO: 138:

AAGACCTCAA GGTAGAAAAA                                                  20

(2) INFORMATION FOR SEQ ID NO: 139:

(i) SEQUENCE CHARACTERISTICS:
         (A) LENGTH: 29
         (B) TYPE: Nucleic Acid
         (C) STRANDEDNESS: Single
         (D) TOPOLOGY: Linear (iv) ANTI-SENSE: No (xi) SEQUENCE DESCRIPTION:  SEQ ID NO: 139:

ACGGGGAGTC GGGGCTGCCA GAGAGAAGT                                        29
```